US011887622B2

(12) United States Patent
Hu et al.

(10) Patent No.: US 11,887,622 B2
(45) Date of Patent: Jan. 30, 2024

(54) MENTAL HEALTH DIAGNOSTICS USING AUDIO DATA

(71) Applicant: The MITRE Corporation, McLean, VA (US)

(72) Inventors: Qian Hu, Lexington, MA (US); Brian P. Marx, Sharon, MA (US); Patricia D. King, Hampton, NH (US); Seth-David Donald Dworman, Bedford, MA (US); Matthew E. Coarr, Newton, MA (US); Keith A. Crouch, Cambridge, MA (US); Stelios Melachrinoudis, Framingham, MA (US); Cheryl Clark, Arlington, MA (US); Terence M. Keane, Brookline, MA (US)

(73) Assignee: United States Department of Veteran Affairs, Washington, DC (US)

( * ) Notice: Subject to any disclaimer, the term of this patent is extended or adjusted under 35 U.S.C. 154(b) by 0 days.

(21) Appl. No.: 16/569,175

(22) Filed: Sep. 12, 2019

(65) Prior Publication Data

US 2020/0090681 A1    Mar. 19, 2020

Related U.S. Application Data

(60) Provisional application No. 62/731,457, filed on Sep. 14, 2018.

(51) Int. Cl.
*G10L 25/66*       (2013.01)
*G10L 25/90*       (2013.01)
(Continued)

(52) U.S. Cl.
CPC ............... *G10L 25/66* (2013.01); *A61B 5/16* (2013.01); *A61B 5/4803* (2013.01);
(Continued)

(58) Field of Classification Search
CPC ......... G10L 25/18; G10L 25/63; G10L 25/66; G10L 25/90; G10L 17/00; A61B 5/16;
(Continued)

(56) References Cited

U.S. PATENT DOCUMENTS

2004/0249634 A1 * 12/2004 Degani ............... G10L 17/26
704/207
2012/0116186 A1 * 5/2012 Shrivastav ........... A61B 5/4803
600/301
(Continued)

FOREIGN PATENT DOCUMENTS

CN       106725532       5/2017
WO       2016/028495     2/2016

OTHER PUBLICATIONS

"Computer scientists learn the language patterns of psychiatric disorders", (Apr. 2016) National Institutes of Health located at <https://obssr.od.nih.gov/computer-scientists-learn-the-language-patterns-of-psychiatric-disorders/> (3 pages).
(Continued)

*Primary Examiner* — Pierre Louis Desir
*Assistant Examiner* — Nicole A K Schmieder
(74) *Attorney, Agent, or Firm* — Morrison & Foerster LLP

(57) ABSTRACT

The present disclosure generally relates to a system and method for obtaining a diagnosis of a mental health condition. An exemplary system can receive an audio input; convert the audio input into a text string; identify a speaker associated with the text string; based on at least a portion of the audio input, determine a predefined audio characteristic of a plurality of predefined audio characteristics; based on the determined audio characteristic, identify an emotion corresponding to the portion of the audio input; generate a set of structured data based on the text string, the speaker, the predefined audio characteristic, and the identified emo-
(Continued)

tion; and provide an output for obtaining the diagnosis of the mental disorder or condition, wherein the output is indicative of at least a portion of the set of structured data.

**17 Claims, 15 Drawing Sheets
(11 of 15 Drawing Sheet(s) Filed in Color)**

(51) Int. Cl.
| | |
|---|---|
| *G10L 25/63* | (2013.01) |
| *A61B 5/00* | (2006.01) |
| *A61B 5/16* | (2006.01) |
| *G10L 17/00* | (2013.01) |
| *G10L 25/18* | (2013.01) |

(52) U.S. Cl.
CPC .......... *A61B 5/7267* (2013.01); *A61B 5/7282* (2013.01); *G10L 17/00* (2013.01); *G10L 25/18* (2013.01); *G10L 25/63* (2013.01); *G10L 25/90* (2013.01)

(58) Field of Classification Search
CPC .... A61B 5/4803; A61B 5/7267; A61B 5/7282
USPC ......................................................... 704/235
See application file for complete search history.

(56) References Cited

U.S. PATENT DOCUMENTS

| | | | |
|---|---|---|---|
| 2012/0221251 A1 | 8/2012 | Rosenberg et al. | |
| 2015/0287402 A1* | 10/2015 | Okabe | G10L 15/08 704/249 |
| 2015/0318002 A1 | 11/2015 | Karam et al. | |
| 2017/0084295 A1* | 3/2017 | Tsiartas | G10L 17/02 |
| 2017/0251985 A1 | 9/2017 | Howard | |
| 2018/0331990 A1* | 11/2018 | Bastide | H04L 51/10 |
| 2019/0180871 A1* | 6/2019 | Doerflinger | G16H 50/20 |

OTHER PUBLICATIONS

Matheson (Jan. 2016) "Watch your tone Voice-analytics software helps customer-service reps build better rapport with customers," located at <http://news.mit.edu/2016/startup-cogito-voice-analytics-call-centers-ptsd-0120> (4 pages).

Mullin (Jan. 2017) "Voice Analysis Tech Could Diagnose Disease," located at <https://www.technologyreview.com/s/603200/voice-analysis-tech-could-diagnose-disease> (5 pages).

* cited by examiner

MENTAL HEALTH DIAGNOSTICS USING AUDIO DATA

RELATED APPLICATIONS

This application claims priority to U.S. Provisional Application Ser. No. 62/731,457, filed Sep. 14, 2018, entitled "MENTAL HEALTH DIAGNOSTICS USING AUDIO DATA," which is incorporated herein in its entirety.

STATEMENT REGARDING FEDERALLY-SPONSORED RESEARCH

This research was supported by the Department of Veterans Affairs including salary support and other research resources provided by the VA National Center for Post-Traumatic Stress Disorder.

FIELD OF INVENTION

The present disclosure relates generally to medical diagnostics, and more specifically to computerized techniques for diagnosing mental health conditions such as PTSD based on audio data.

BACKGROUND

Posttraumatic Stress Disorder (PTSD) is one of the most common psychiatric disorders affecting veterans. To ensure appropriate treatment and maximize recovery, accurate diagnosis is imperative. PTSD diagnosis is currently based on symptoms self-reported by a patient using either a self-report questionnaire or a clinician administered interview. During a clinical interview, the preferred method of determining diagnostic status, the clinician uses the patient's description of the symptoms to reach a diagnostic determination.

However, the verbal descriptions of a patient may not be an accurate reflection of the patent's mental state. The patient can over-emphasize or under-emphasize his or her experiences in the narrative. Thus, a literal interpretation of the patient's descriptions alone, without considering the non-verbal cues, may lead to over-diagnosis or under-diagnosis. Further, a clinician's interpretation of non-verbal cues may be subjective, inaccurate, and unquantifiable. Although having multiple clinicians interview a patient or evaluate an interview can result in a diagnosis in which we have greater confidence, doing so can be time-consuming and prohibitively expensive.

Thus, there is a need for techniques for obtaining objective, consistent, and accurate diagnosis of mental conditions such as PTSD without incurring significant operational cost. These techniques should rely on objective metrics of verbal and non-verbal cues from the patient rather than relying on a clinician's interpretation of the patient's mental state.

BRIEF SUMMARY

In some embodiments, a computer-enabled method for obtaining a diagnosis of a mental health condition comprises: receiving an audio input; converting the audio input into a text string; identifying a speaker associated with the text string; based on at least a portion of the audio input, determining a predefined audio characteristic of a plurality of predefined audio characteristics; based on the determined audio characteristic, identifying an emotion corresponding to the portion of the audio input; generating a set of structured data based on the text string, the speaker, the predefined audio characteristic, and the identified emotion; and providing an output for obtaining a diagnosis of a mental health condition, wherein the output is indicative of at least a portion of the set of structured data.

In some embodiments, an exemplary electronic device comprises a display; one or more processors; a memory; and one or more programs. The one or more programs are stored in the memory and configured to be executed by the one or more processors, the one or more programs including instructions for: receiving an audio input; converting the audio input into a text string; identifying a speaker associated with the text string; based on at least a portion of the audio input, determining a predefined audio characteristic of a plurality of predefined audio characteristics; based on the determined audio characteristic, identifying an emotion corresponding to the portion of the audio input; generating a set of structured data based on the text string, the speaker, the predefined audio characteristic, and the identified emotion; and providing an output for obtaining a diagnosis of a mental health condition, wherein the output is indicative of at least a portion of the set of structured data.

In some embodiments, an exemplary non-transitory computer-readable storage medium stores one or more programs. The one or more programs comprises instructions, which when executed by one or more processors of an electronic device having a display, cause the electronic device to: receive an audio input; convert the audio input into a text string; identify a speaker associated with the text string; based on at least a portion of the audio input, determine a predefined audio characteristic of a plurality of predefined audio characteristics; based on the determined audio characteristic, identify an emotion corresponding to the portion of the audio input; generate a set of structured data based on the text string, the speaker, the predefined audio characteristic, and the identified emotion; and provide an output for obtaining a diagnosis of a mental health condition, wherein the output is indicative of at least a portion of the set of structured data.

DESCRIPTION OF THE FIGURES

The patent or application file contains at least one drawing executed in color. Copies of this patent or patent application publication with color drawings will be provided by the office upon request and payment of the necessary fee.

FIG. 2A depicts exemplary user interfaces of an electronic device in accordance with some embodiments.

FIG. 2B depicts exemplary user interfaces of an electronic device in accordance with some embodiments.

FIG. 7 depicts exemplary user interfaces of an electronic device in accordance with some embodiments.

DETAILED DESCRIPTION

Figure 1A:
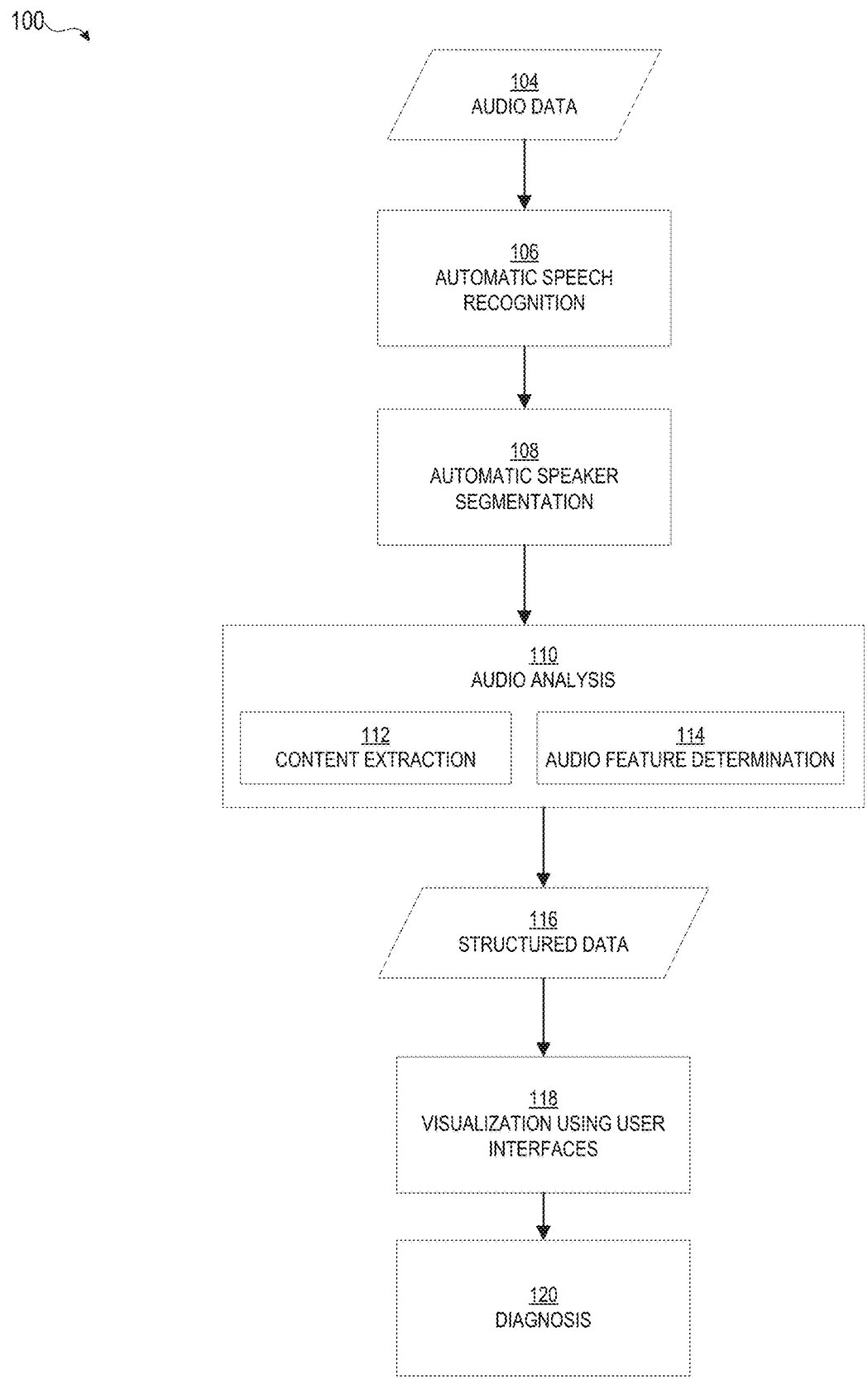
FIG. 1A depicts an exemplary process for processing audio data to diagnose mental health conditions, in accordance with some embodiments.

The present invention includes systems and methods for obtaining objective and accurate diagnosis of mental conditions based on verbal and non-verbal cues, without incurring significant operational cost. Specifically, the present invention includes computerized techniques for automatically processing audio data associated with patient interviews, identifying non-verbal and verbal indicators of the mental condition from the audio data, and providing user interfaces for clinicians to search and retrieve indicators to perform quantitative and qualitative analysis and reach a diagnosis. This way, the computerized techniques help to obtain objective, consistent, and accurate diagnostic results (e.g., PTSD) that are more objective, consistent and accurate than diagnosis based solely on the judgement of a clinician, without incurring significant operational cost.

In some embodiments, by combining specific content the patient talks about during the interviews with the audio characteristics identified from the interviews, the system allows the clinician to quickly and systematically identify indicators of a mental health condition from single or multiple interviews to confer a diagnosis. After the system processes the interview audio and extracts the relevant information, the system allows the same interview to be analyzed for diagnosis by a single doctor or a group of doctors at any time and provides user interfaces to present rich information about the interview.

In some embodiments, the speech-based diagnosis of mental health conditions can be performed during or after routine checkups, thus providing non-invasive, cost-effective, and timely monitoring of the individual mental health condition. In some embodiments, the speech-based diagnosis can be performed to screen for high risk factors before, during, and after military service for prevention, early diagnosis, and treatment.

The following description is presented to enable a person of ordinary skill in the art to make and use the various embodiments. Descriptions of specific devices, techniques, and applications are provided only as examples. Various modifications to the examples described herein will be readily apparent to those of ordinary skill in the art, and the general principles defined herein may be applied to other examples and applications without departing from the spirit and scope of the various embodiments. Thus, the various embodiments are not intended to be limited to the examples described and shown herein, but are to be accorded the scope consistent with the claims. For example, the various embodiments are not intended to be limited to diagnosis of PTSD, but are applicable to diagnosis of other mental health conditions.

Although the following description uses terms "first," "second," etc. to describe various elements, these elements should not be limited by the terms. These terms are only used to distinguish one element from another. For example, a first format could be termed a second format, and, similarly, a second format could be termed a first format, without departing from the scope of the various described embodiments. The first format and the second format are both formats, but they are not the same format.

The terminology used in the description of the various embodiments described herein is for the purpose of describing particular embodiments only and is not intended to be limiting. As used in the description of the various described embodiments and the appended claims, the singular forms "a," "an," and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

The term "if" is, optionally, construed to mean "when" or "upon" or "in response to determining" or "in response to detecting," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]," depending on the context.

FIG. 1A depicts an exemplary process for processing audio data to diagnose mental health conditions, in accordance with some embodiments. Process 100 is performed, for example, using one or more electronic devices implementing a diagnostic system. In some examples, process 100 is performed using a client-server system, and the blocks of process 100 are divided up in any manner between the server and a client device. In other examples, the blocks of process 100 are divided up between the server and multiple client devices. Thus, although portions of process 100 are described herein as being performed by particular devices of a client-server system, it will be appreciated that process 100 is not so limited. In other examples, process 100 is performed using only a client device or only multiple client devices. In process 100, some blocks are, optionally, combined, the order of some blocks is, optionally, changed, and some blocks are, optionally, omitted. In some examples, additional steps may be performed in combination with the process 100. Accordingly, the operations as illustrated (and described in greater detail below) are exemplary by nature and, as such, should not be viewed as limiting.

With reference to FIG. 1A, a system receives audio data 104. The audio data captures a conversation between one or more interviewers (e.g., clinicians) and one or more patients (e.g., veterans) being evaluated for mental health conditions (e.g., PTSD). In some embodiments, the conversation captured in the audio data has already taken place in the past, and the audio data 104 includes one or more audio files. In some embodiments, the conversation captured by the audio data is ongoing, and the audio data 104 includes a stream of audio signals sampled by one or more microphones.

The audio data 104 can include speech from multiple speakers (e.g., clinicians, patients). The audio data 104 can further include verbal and non-verbal information. For example, the audio data 104 can include verbal utterances such as "I can't sleep," "I don't want to talk about it," "I don't remember," and "I have nightmares." Additionally, the audio data 104 can include non-verbal information, such as varying speech rates and energy levels, silences, and pauses.

In some embodiments, the audio data 104 is converted into a standard format before being further processed. The audio data 104 can be originally stored in a first format (e.g., based on the hardware and/or software used to sample the audio data), and then converted into a second format. In some examples, the audio data 104 is converted into one or more RAW files having the .pcm extension before being further processed.

At step 106, automatic speech recognition ("ASR") is performed to convert the speech captured in the audio data 104 into text. In some embodiments, the audio data 104 is converted into a text string. The speech recognition can be performed using commercial off-the-shelf algorithms, an open-source ASR software development kit ("SDK"), or a combination thereof. In some embodiments, different acoustic models can be selected based on the patient being interviewed. In some embodiments, the ASR algorithms have been trained based on previous patient interviews (e.g., PTSD interviews). In some embodiments, the ASR algorithms use lexicons specific to certain mental diseases (e.g., PTSD).

In some embodiments, the step 106 is initiated in response to a user input (e.g., the user selects an audio file and issues a request to initiate the ASR process). In some embodiments, the step 106 is initiated automatically in response to a triggering event (e.g., a microphone starts sampling audio signals from an ongoing conversation). In some embodiments, the system allows the user to specify relevant parameters (e.g., gender of the speakers, acoustic models to be used, detection/extraction algorithms to be used) before further recording and/or processing the audio data. An exemplary user interface is described with reference to FIG. 7 below.

At step 108, automatic speaker segmentation is performed to identify the speakers in the audio data 104. For example, the system can automatically identify portions of the audio data 104 as corresponding to the patient's speech and portions of the audio data 104 as corresponding to the clinician's speech. The segmentation can be performed using government off-the-shelf algorithms, an open-source diarization SDK, or a combination thereof. Based on the segmentation, the system can determine the total amount of speech each speaker produced during the interview. Further, the segmented speech can be used to identify speech characteristics of PTSD patients and doctors (e.g., via machine learning), as discussed in detail below.

In some embodiments, the system performs automatic indexing of all words spoken by all speakers during the interview. For example, the system can associate each syllable, each word, each phrase, and/or each sentence with a speaker ID, a time stamp, and a duration value. Additional metadata (e.g., emotion, speech rate) can be associated to the words, as discussed in detail below.

At step 110, audio analysis is performed. Specifically, the system can analyze both verbal and non-verbal aspects of the conversation captured in audio data 104 to identify indicators of a mental disorder. For PTSD, the common indicators include intrusive symptoms, avoidance of thoughts and behaviors, negative cognitions and mood, and alterations in arousal and reactivity.

As depicted in FIG. 1A, the audio analysis 110 includes both content extraction 112 (e.g., what was said) and audio feature determination 114 (e.g., how it was said). During content extraction 112, verbal cues are derived from the recognized text strings. During audio feature determination 114, non-verbal cues are derived from the audio characteristics of the recording (e.g., volume, pitches). In some examples, the results from content extraction 112 and audio feature determination 114 can be correlated and/or aggregated to obtain additional rich information about the patient's state of mind.

The content extraction 112 can include extraction of PTSD-indicative words, phrases, and descriptions. In some embodiments, the system can look for the presence of one or more predefined words in the recognized text strings, such as "nightmare," "stressed," "trouble sleeping," "upset," and pronouns. In some embodiments, the system uses one or more trained classifiers to identify a verbal description as a PTSD indicator. For example, the system can identify sentences uttered by the patients that suggest to self-harm, suicide, sleep disorders, avoidance of certain activities that are reminiscent of the traumatic experience, detachment from reality, etc. In some embodiments, the classifiers are neural network classifiers trained on data (e.g., previous interviews with veterans coping with PTSD) from various data sources. In some embodiments, the system uses the clinician's questions to guide the detection of PTSD indicators. For example, if the clinician asks, "Do you feel anxious," the text strings corresponding to the patient's response may be associated with the topic of "anxiety." In some embodiments, the system indexes the recognized text strings with the extracted PTSD indicators. For example, the system can associate a sentence with a tag or keyword "self-harm" or "avoidance."

In some embodiments, the content extraction 112 includes the extraction of patterns. For example, the system can analyze the recognized text strings to determine: words/phrases/topics frequently mentioned by the speaker, words/phrases/topics frequently emphasized by the speaker, closely associated words/phrases/topics (e.g., topics that are mentioned in proximity to each other), abrupt change of topics, etc. For example, a heavy use of pronouns rather than nouns can indicate speech impediment.

In some embodiments, the content extraction 112 includes type-token analysis and a summary algorithm to show the ratio of total number of unique words (type) used as compared with total number of words (frequency/token) used by a speaker. In some embodiments, the content extraction 112 includes analysis of how much each speaker talks in the conversation, for example, in terms of time and word count.

In some embodiments, the content extraction 112 includes identification of content that a speaker has failed to utter or utter properly. For example, a speaker may fail to enunciate particular words. The system can detect the speaker's failure to enunciate a word based on, for example, a low confidence score assigned to the word during the speech recognition process. As another example, the speaker may purposely avoid uttering certain words or phrases even though these words or phrases are commonly used in relation to certain scenarios (e.g., description of war). Accordingly, the system can flag the absence of these words or phrases.

The audio feature determination 114 can include automatic detection of speech rate. The system can further measure how the speech rate deviates from the normal range of an average speaker. For example, the system can determine that a speech rate is abnormally high compared with an average speaker if the speech rate is higher than a predetermined threshold value. In addition, the system can measure how the speech rate deviates from the speaker's average speech rate. For example, the system can determine that a speech rate is abnormally high for the speaker if the speech rate is higher than the average speech rate of the speaker during the conversation.

In some embodiments, the audio feature determination 114 can include automatic detection of other audio characteristics such as pitch, intonation, or energy level (e.g., volume) in the speech production.

In some embodiments, the audio feature determination 114 can include identification of emotions. The identification of emotions can be performed by detecting audio characteristics often associated with certain types of emotional states or levels of mental vigilance. For example, when the speaker's speech rate deviates significantly from his/her normal speech rate, it indicates a change of emotional or mental state. Faster than normal speech rate can be indicative of emotions such as vigilance or excitement. In addition to speech rate, the person's vocal effort such as pitch, intonation, energy level in the speech production can also indicate the person's emotional and psychological state.

In some embodiments, emotions can be extracted from non-verbal cues such as pauses, sighs, coughs, heavy breathing. For example, a long pause can indicate difficulty with articulation or distress. Emotions can further be extracted from filler words (e.g., "umm," "you know"). For example, a large number of filler words can indicate difficulty with articulation, hesitation, or uncertainness.

In some embodiments, the results from the content extraction 112 and the audio characteristics 114 can be aggregated and correlated to uncover rich information. For example, the system can identify that certain words/phrases/topics (e.g., the topic of war) are associated with certain emotions (e.g., distress). As another example, the system can detect an increasing level of emotion (e.g., anger) in response to answering the same question more than once during the conversation. As another example, the system can detect events such as false starts, avoidance, restarts, and self-correction in the speaker's response to certain questions. The events can be detected based on a combination of verbal and non-verbal cues. For example, a formulation " . . . can can't remember [pause] . . . " may indicate a false start; a formulation " . . . it eh eh it was [pause] too long ago . . . " or a formulation " . . . [pause] I don't want to talk about it . . . " may indicate avoidance.

Based on the audio analysis performed at step 110, the system generates structured data 116. All identified information (e.g., speech rates, emotions) can be structured and stored accordingly to enable cross-modality search and retrieval. In some embodiments, the system time-aligns the transcript (i.e., the recognized text strings) with the streaming of the audio or video. For example, the system can establish mappings between words in the transcript with timestamps of the audio. In some embodiments, the system allows for the metadata entry and association of the metadata with the processed audio files and the transcript. For example, the system can associate all identified information (e.g., emotion, pitch, keyword, avoidance) in step 110 with a portion of the recognized text strings and/or a portion of the audio data 104. In some embodiments, the structured data 116 includes relationships among the identified information. For example, the structured data 116 can establish relationships among synonymous words/phrases (i.e., semantic expansion). As another example, the structured data 116 can establish correlations between identified information and the corresponding questions from the interviewer. In summary, the structured data 116 can inform the critical issues of "Who said What," "When," "How was it said," "In what context," and "In what emotional state," which in turn can lead to an objective diagnosis of PTSD.

At step 118, visualization of the structured data 118 is provided via one or more user interfaces. The user interfaces enable the search of the structured data 118 and the display of the search results. In some embodiments, the user interfaces are provided via a web portal. Exemplary user interfaces are described below with reference to FIGS. 2A-6.

At step 120, clinicians can use the user interfaces to obtain an evidence-based and systematic understanding of the patient's state of mind to determine diagnosis. For example, the clinician can retrieve all the segments from the entire interview when the patient spoke about sleeping disorder or other symptoms. The clinician can then listen to this specific segment when the patient was describing his/her sleep condition. As another example, the user interfaces allow the clinician to search for and retrieve certain features and expressions from all the interviews with a single patient or with a group of patients for diagnostic analysis and decision making. In some embodiments, a predicted diagnosis can be automatically provided by the system.

Figure 1B:
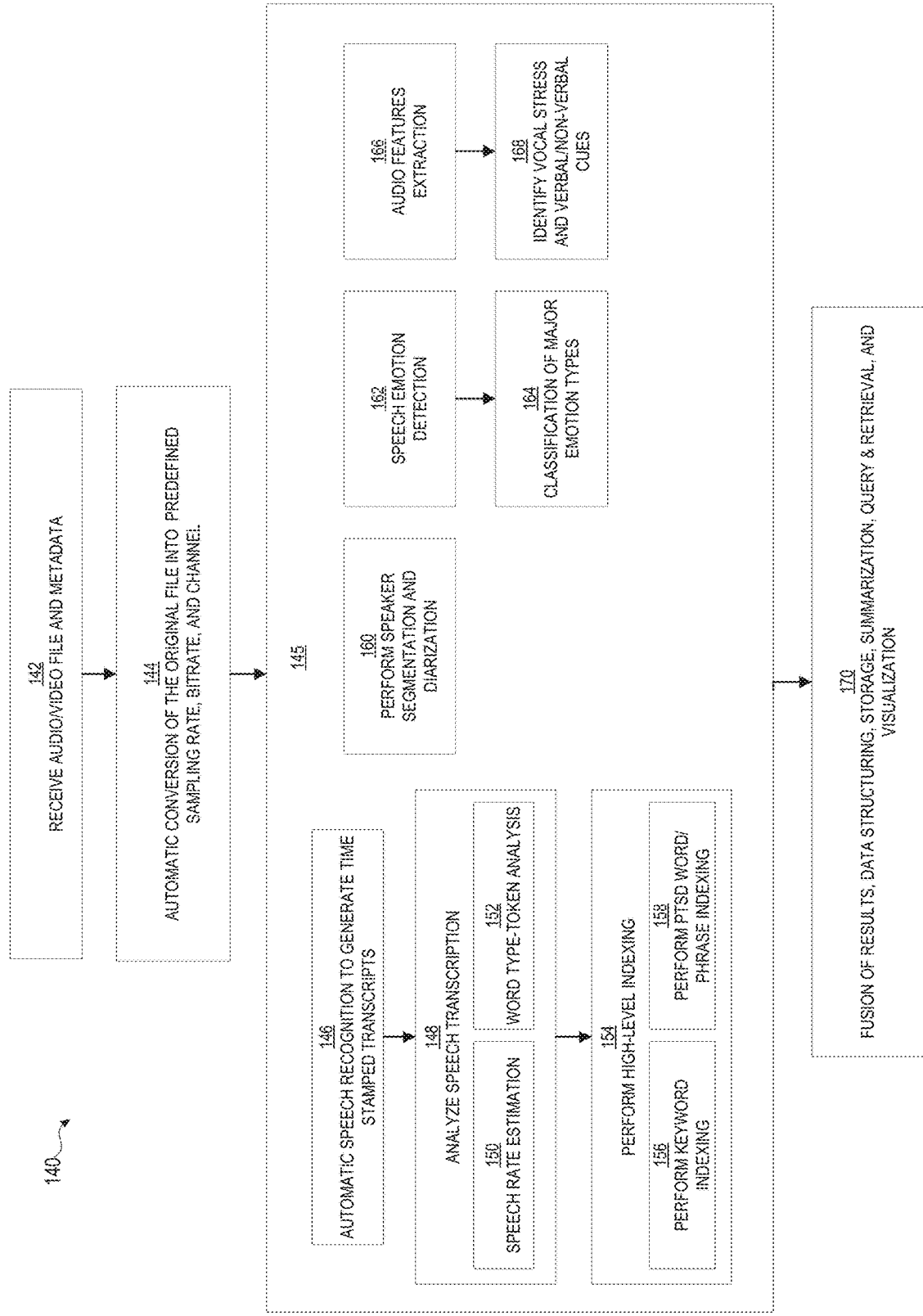
FIG. 1B depicts an exemplary process for processing audio data to diagnose mental health conditions, in accordance with some embodiments.

FIG. 1B depicts an exemplary process 140 for processing audio data to diagnose mental health conditions, in accordance with some embodiments. Process 140 is performed, for example, using one or more electronic devices implementing a diagnostic system. In some examples, process 140 is performed using a client-server system, and the blocks of process 140 are divided up in any manner between the server and a client device. In other examples, the blocks of process 140 are divided up between the server and multiple client devices. Thus, while portions of process 140 are described herein as being performed by particular devices of a client-server system, it will be appreciated that process 140 is not so limited. In other examples, process 140 is performed using only a client device or only multiple client devices. In process 140, some blocks are, optionally, combined, the order of some blocks is, optionally, changed, and some blocks are, optionally, omitted. In some examples, additional steps may be performed in combination with the process 140. Accordingly, the operations as illustrated (and described in greater detail below) are exemplary by nature and, as such, should not be viewed as limiting.

With reference to FIG. 1B, at block 142, a system receives audio data. The audio data can be the same as the audio data 104 described above with reference to FIG. 1A. The audio data can be part of one or more audio files and/or video files. The audio data captures a conversation between one or more interviewers (e.g., doctors) and one or more patients (e.g., veterans) being evaluated for mental health conditions (e.g., PTSD).

At block 142, the system can also receive metadata associated with the interview. The metadata can include any information associated with interview, such as information specifying the time of recording, the environment in which the recording was made (e.g., location, level of noise, setting), number of speakers, characteristics or histories of the speakers, or a combination thereof.

Figure 7:
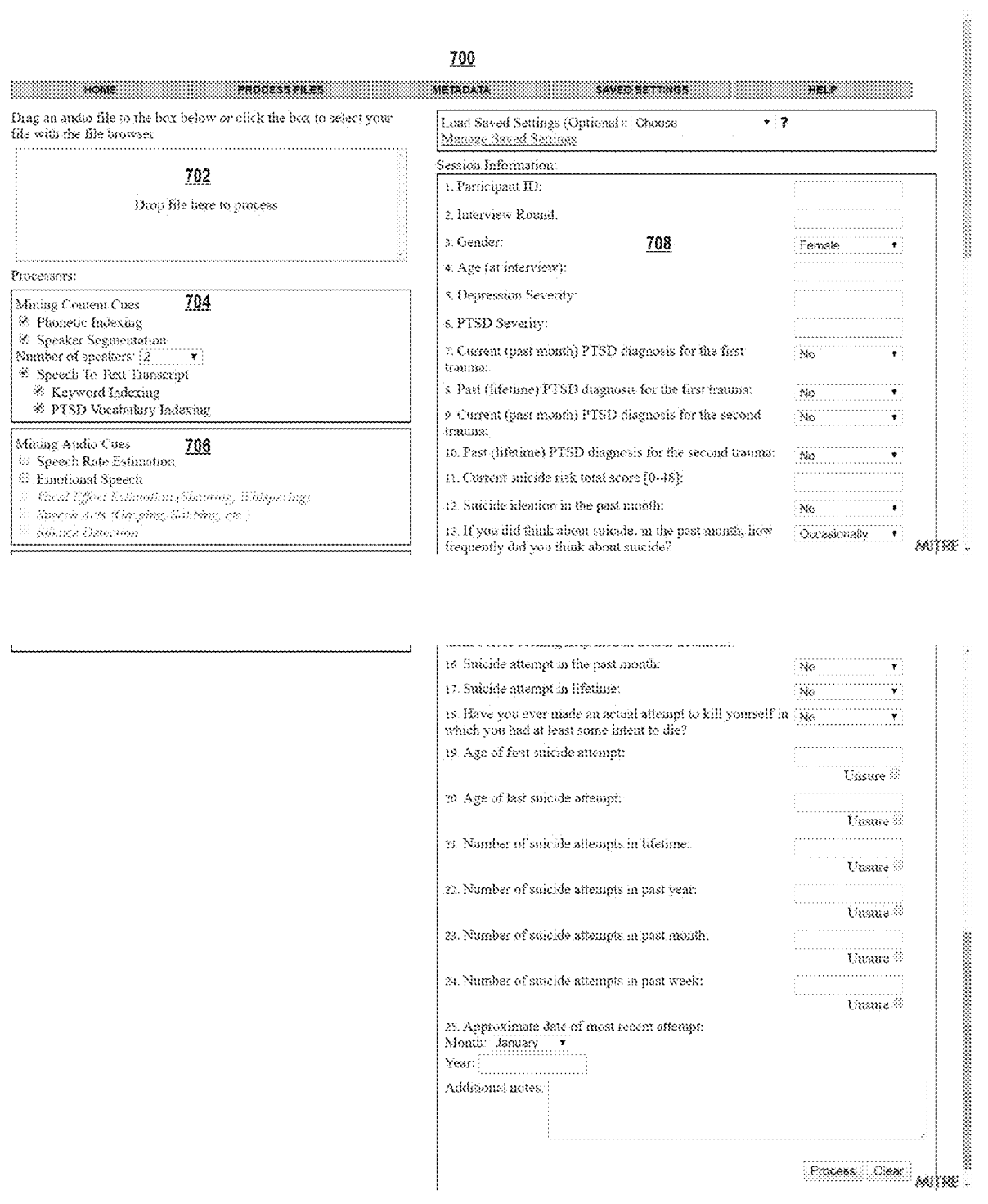

FIG. 7 depicts an exemplary user interface 700 for receiving a file and metadata. As shown, the user interface 700 includes a user affordance 702 that allows the user to drag and drop a file for processing. The user interface 700 also includes a user affordance 708 that allows the user to specify information related to the patient. As shown, the information related to the patient can include: participant ID, gender, age, depression severity, PTSD severity, current PTSD diagnosis for the first trauma, etc.

The metadata can be later retrieved and reviewed by a clinician to provide additional context for obtaining a diagnosis. Further, the metadata can be used by the system to process the audio/video file. For example, information related to the patient and other speakers can be used to help the system in terms of speech recognition, speaker segmentation, and emotion detection.

In some embodiments, the system can also receive one or more user commands regarding the types of processing to be performed on the file. As shown in FIG. 7, user affordances 704 and 706 allow the user to specify the types of processing to be performed on the file. Exemplary types of processing include: phonetic indexing, speaker segmentation, speech-to-text transcription, keyword indexing, PTSD vocabulary indexing, speech rate estimation, emotion detection, vocal effort estimation, speech acts detection, and silence detection.

Returning to FIG. 1B, at block 144, the system converts the received file according to predefined parameters, such as sampling rate, bitrate, and channel. For example, the file can be down-sampled to 8 kHz. The predefined parameters can be determined based on the subsequent processing algorithms (e.g., ASR) to be used.

At block 145, one or more types of processing can be performed on the converted file. The types of processing can be specified by the user, for example, via the user interface 700 depicted in FIG. 7. In some embodiments, the types of processing can be automatically determined by the system. For example, if the user has specified that the interview has multiple speakers, the system may automatically perform speaker segmentation. As another example, if the user has specified that the patient has been previously diagnosed with certain diseases, the system may automatically index keywords associated with those diseases (e.g., keywords known to be associated with depression).

At block 146, the system performs ASR to generate time-stamped transcripts. As discussed above, the system can associate elements in the transcript (e.g., syllables, words, phrases, sentences) with time stamps. For example, the beginning and end of each word can be time-stamped. In some embodiments, the system associates confidence scores with recognized elements in the transcript. The confidence score can be determined based on, for example, phonetic similarity and context.

At block 148, the system analyzes the speech transcription. The analysis can include speech rate estimation 150 and/or word type-token analysis 152. The speech rate can be expressed as the number of syllables or vowels uttered by a speaker during a period of time. As discussed above, the system can further measure how the speech rate deviates from the normal range of an average speaker. In some embodiments, the system allows the user to specify what constitutes a normal range, a fast range, or a slow range.

The word type-token analysis 152 can comprise determining the ratio between the number of unique words (excluding certain words such as articles) and the total number of words uttered by a speaker. The ratio can be indicative of the education level and/or the cognitive capability of the speaker. The system can further measure how the ratio deviates from the normal range (e.g., a speaker having an average education level and possessing average cognitive capability).

At block 154, the system performs high-level indexing, which can include keyword indexing 156 and/or PTSD word/phrase indexing 158. As part of keyword indexing 156, the system identifies and indexes certain categories of words, such as nouns, adjectives, and/or adverbs. The system may exclude certain categories of words (e.g., articles) from indexing. As part of PTSD word/phrase indexing, the system identifies and indexes predefined words or phrases that are known to be correlated with PTSD or symptoms of PTSD. Exemplary PTSD keywords are provided in FIGS. 2C and 4F.

At block 160, the system performs speaker segmentation and diarization. As discussed above, speaker segmentation is performed to identify the different speakers in the audio data. In some embodiments, the system automatically assigns an identifier (e.g., 0-N) to each of the identified speakers.

At block 162, the system performs speech emotion detection. In some embodiments, standard off-the-shelf emotion detection algorithms are used. In some embodiments, the system trains or adjusts the emotion detection algorithms based on previous patient interviews. At block 164, the system performs classification of major emotion types, such as anger, sadness, happiness, fear, and neutral.

At block 166, the system performs audio feature extraction. Exemplary audio features include loudness, pitch, energy level, intonation, cepstral, etc. At block 168, the system can identify vocal stress and verbal/non-verbal cues.

At block 170, the system performs fusion of results obtained from blocks 146-168. In some embodiments, the system generates structured data. All identified information (e.g., indexes, speech rate, word type-token ratio, speaker identities, emotions, emotion types, audio features, verbal cues, non-verbal cues) can be structured and stored accordingly to enable cross-modality search and retrieval. For example, the system can associate all identified information with a portion of the recognized text strings and/or a portion of the audio data. In some embodiments, the structured data includes relationships among the identified information. For example, the structured data can establish relationships among synonymous words/phrases (i.e., semantic expansion). As another example, the structured data can establish correlations between identified information and the corresponding questions from the interviewer.

Further, the results from blocks 146-168 can be aggregated and correlated to uncover rich information. For example, the system can identify that certain words/phrases/topics (e.g., the topic of war) are associated with certain emotions (e.g., distress, anger). As another example, the system can identify inconsistencies between what the patient said (e.g., verbal expression of emotions) and how the patient said it (e.g., emotions detected from non-verbal information). In some embodiments, the results from blocks 146-168 are aggregated in a weighted manner. As such, the combination of both lexical and vocal analysis along with the clinical information makes the prediction of PTSD more comprehensive and objective. The four processors interact in such a way that they reinforce one other's analysis and provide a pipeline of output from multiple sources for analysis.

Further, visualization of the structured data is provided via one or more user interfaces. The user interfaces enable querying of the structured data and displaying of the search results. In some embodiments, the user interfaces are provided via a web portal. Exemplary user interfaces are described below with reference to FIGS. 2A-6.

Figures 2A, 2B:
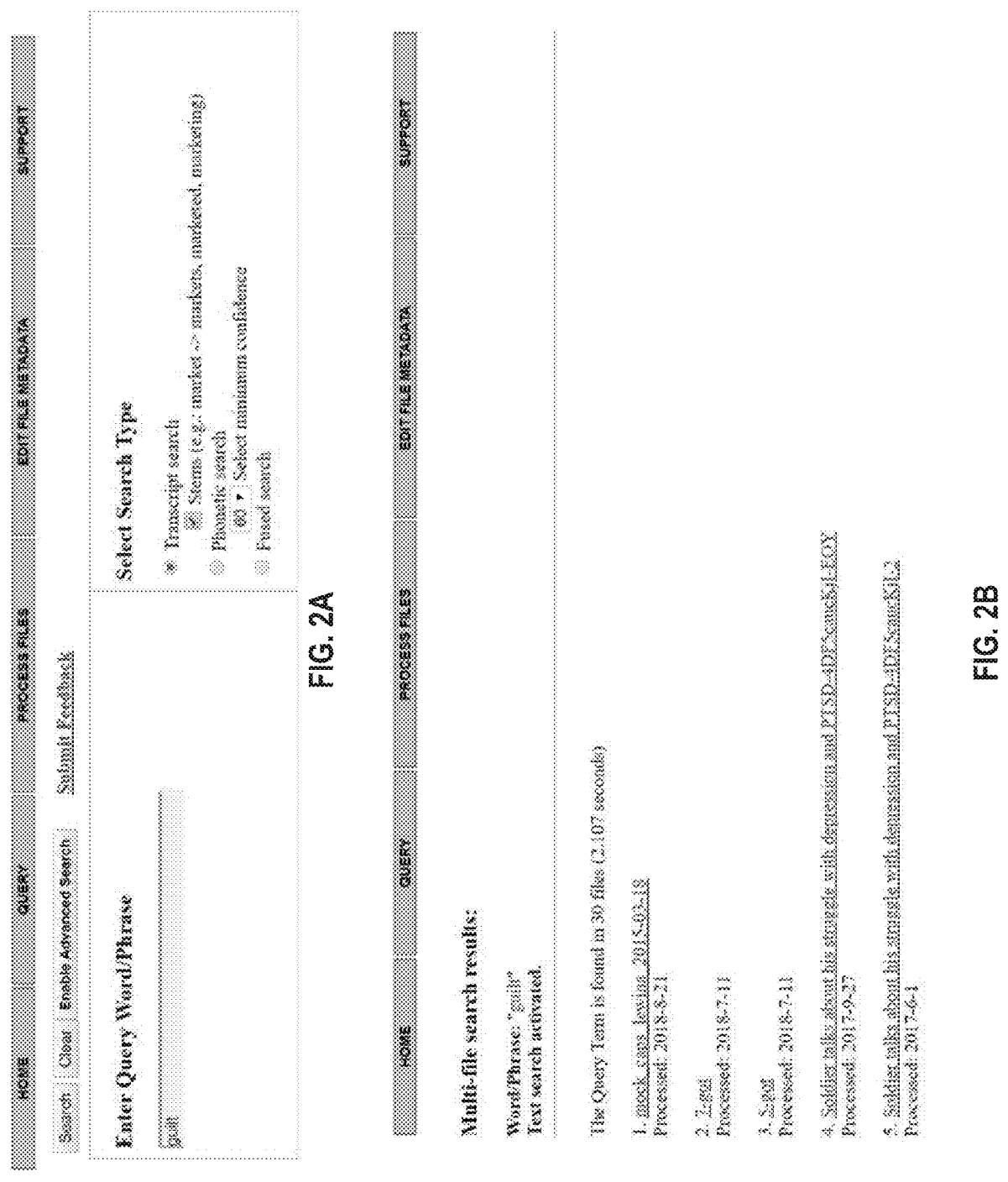

FIG. 2A depicts an exemplary user interface for querying patient interviews from a database, in accordance with some embodiments of the invention. The user interface includes a text box for entering one or more query words or phrases. As depicted, the user has entered a query word "guilt" in the text box.

The user interface also provides user affordances for specifying the type of search to be performed and specific search settings. Transcription search compares the query word(s) with transcripts of the interviews and identify exact matches of spelling and/or semantic expansions/extensions (e.g., stems of the query term, words having similar meanings) of the query word(s). Phonetic search identifies phonetic matches between the query word(s) and the utterances in the interviews. In some embodiments, the user can specify a confidence threshold for the search. Fused search returns results of both transcription search and phonetic search. In some embodiments, the results are ranked based on confidence scores.

As depicted in FIG. 2A, the user has requested a transcript search with semantic extension. An exemplary user interface displaying the search results is shown in FIG. 2B. The search results can include multiple interviews of different patients that meet the search criteria. The user can select a search result, and in response to the selection, a user interface for reviewing the corresponding interview is provided. In some embodiments, the system provides a list of all processed interviews (e.g., via a drop-down menu) such that the user can view and access any processed interview without specifying a keyword.

Figure 2C:
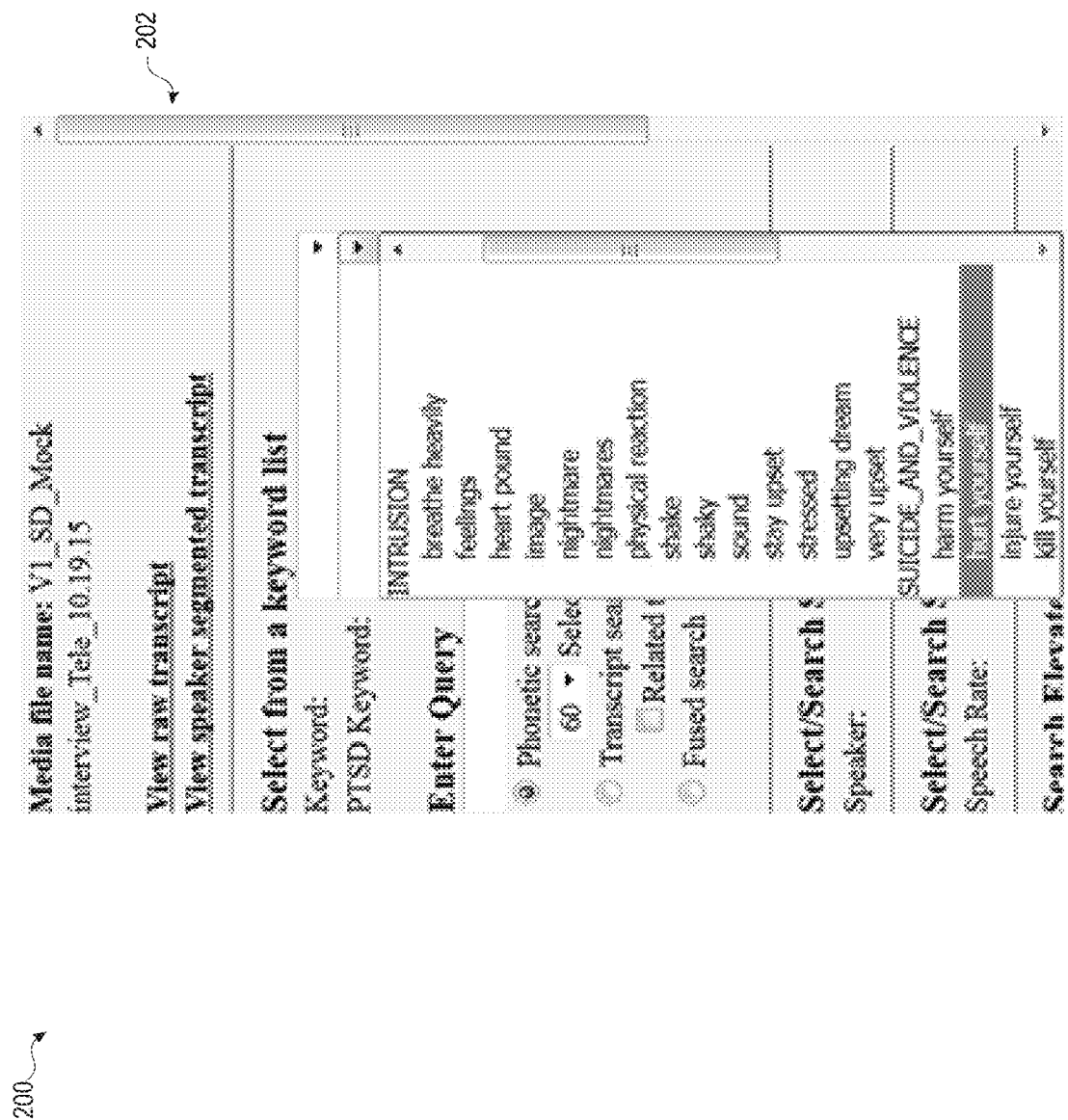
FIG. 2C depicts exemplary user interfaces of an electronic device in accordance with some embodiments.

FIG. 2C depicts a portion of an exemplary user interface 200 for reviewing and exploring a single audio/video interview, in accordance with some embodiments of the invention. The user interface includes a menu panel 202. As depicted, the menu panel displays a plurality of user interface affordances for reviewing the audio interview, such as "View raw transcript" (for viewing text strings recognized from the audio data), "View speaker segmented transcript" (for viewing correlations between speakers and the recognized text strings), "Select from a keyword list," "Enter Query," "Select/Search Speaker," and "Select/Search Speech Rate." Using the menu panel 202, a clinician can review the questions and answers from the interview while exploring different aspects or portions of the interview recording. One of ordinary skill in the art should recognized that any number of additional user affordances can be displayed to allow the user to query the audio data based on content and features described with reference to FIGS. 1A-1B.

As depicted in FIG. 2C, under "Select from a keyword list," the user can select among a plurality of keywords to retrieve corresponding segments of the interview recording. The plurality of keywords can be extracted from the interview recording during the audio analysis step (e.g., step 110 in FIG. 1A or step 154 in FIG. 1B). As discussed above, the extraction of keywords can be based on the content of the patient's speech, the audio features of the patient's speech, the clinician's questions, or a combination thereof. As such, a clinician can view the keywords extracted and easily retrieve the relevant portions of the interview recording for analysis.

In some embodiments, the user interface 200 includes additional panels, for example, to display a control for providing a playback of the audio/video of the interview. In some embodiments, the user interface 200 displays the system's general assessment of the audio interview (e.g., "Negative").

Figure 3:
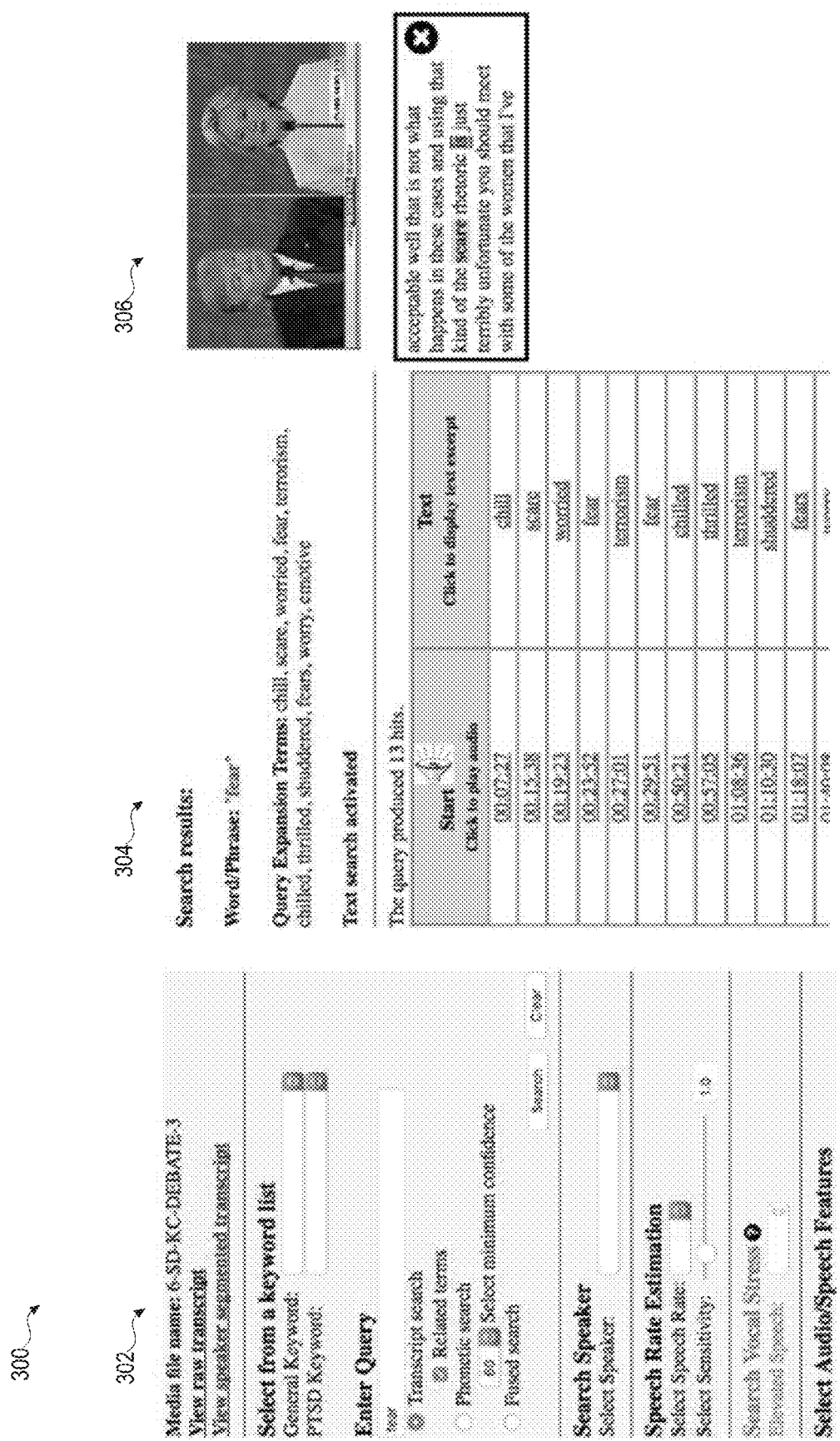
FIG. 3 depicts exemplary user interfaces of an electronic device in accordance with some embodiments.

FIG. 3 depicts an exemplary user interface 300 for reviewing an audio/video interview, in accordance with some embodiments of the invention. The user interface includes a menu panel 302, a main panel 304, and a replay panel 306. Using the "Enter Query" option, a user can conduct a transcript search (e.g., searching based on spelling of the query word), a phonetic search (e.g., searching based on pronunciation of the query word), or a fused search (e.g., searching based on both criteria).

As depicted, the user has entered "fear" as a search term for a transcript search. Further, the user has indicated that the search should also include related terms. In response, the main panel 304 displays search results matching "fear" or a list of synonymous terms "chill," "scare," "worried," "fear," "terrorism," "chilled," "thrilled," "shuddered," "fears," "worry," "emotive." As depicted, the search results include a list of hyperlinked timestamps to provide easy retrieval of the audio segments including the words. If the user selects a hyperlinked timestamp or a hyperlinked word, the replay panel 306 provides the content accordingly. As depicted in FIG. 3, the replay panel 306 provides a playback of the corresponding segment and a display of the speech context containing the corresponding word.

In some embodiments, the user interface 300 further displays various identified information associated with the segment, such as identified speech rate and detected emotion.

Figure 4A:
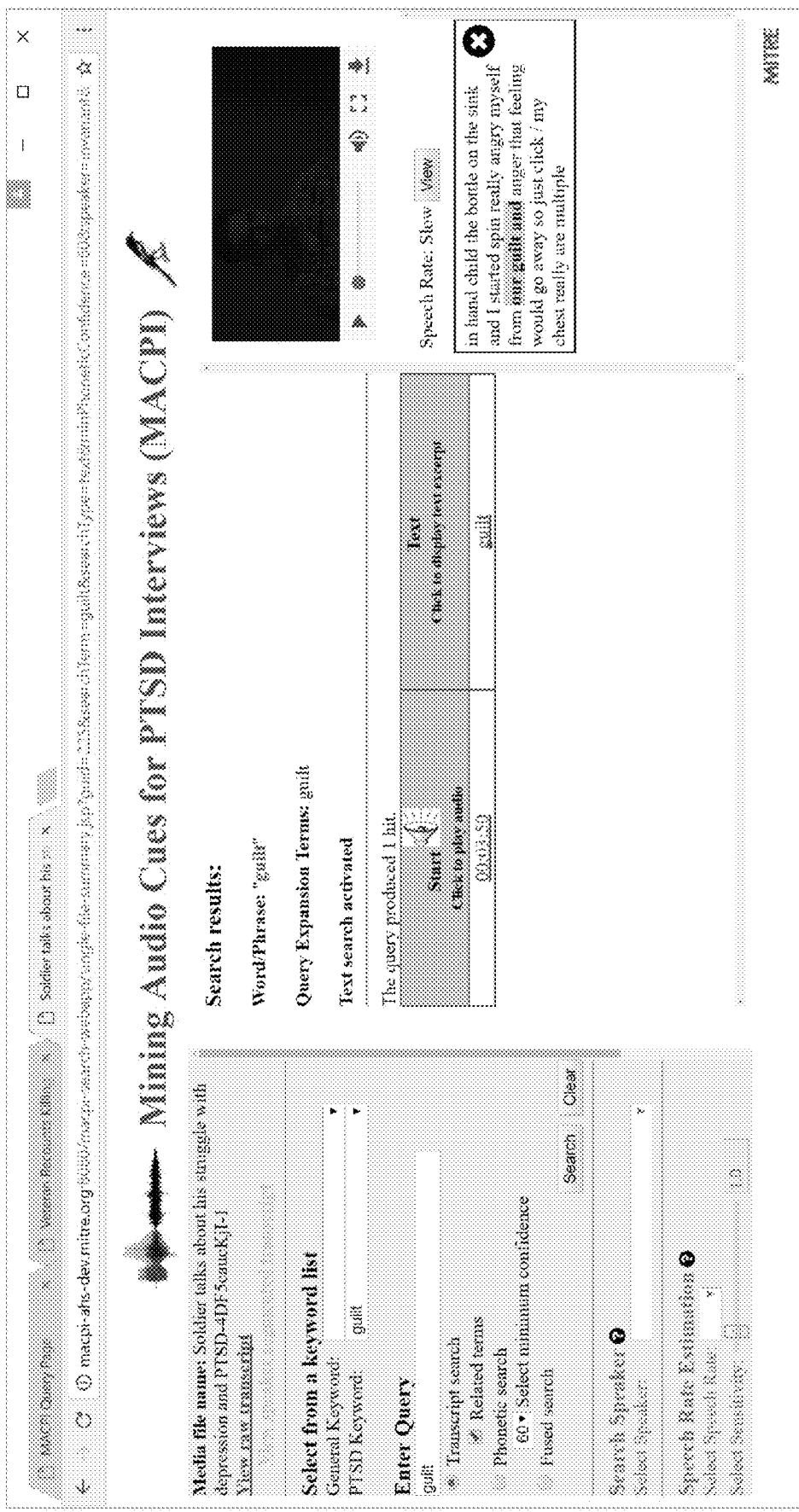
FIG. 4A depicts exemplary user interfaces of an electronic device in accordance with some embodiments.
Figure 4B:
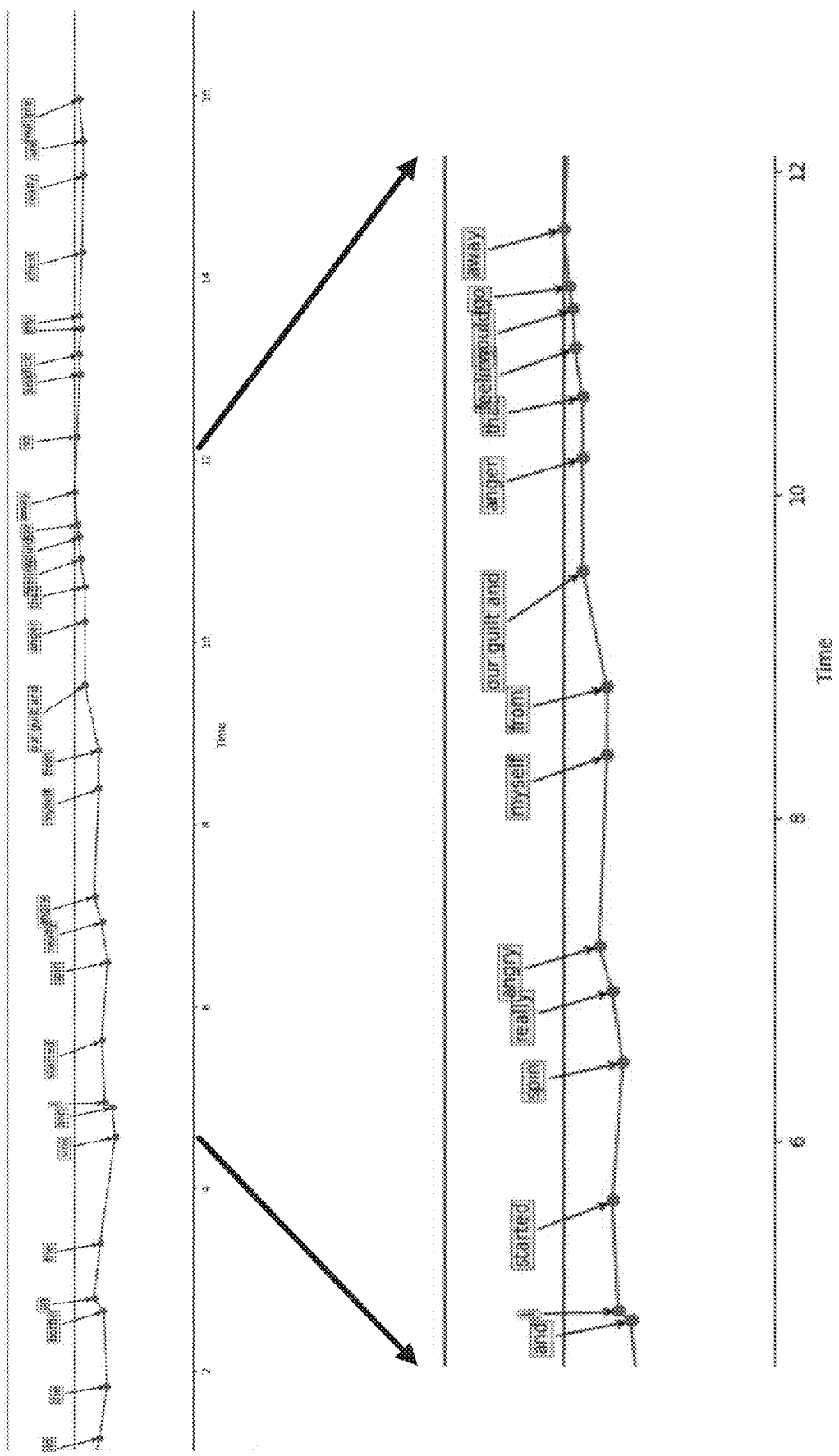
FIG. 4B depicts exemplary user interfaces of an electronic device in accordance with some embodiments.

FIGS. 4A and 4B depict exemplary user interfaces of an electronic device for reviewing an audio/video interview, in accordance with some embodiments of the invention. With reference to FIG. 4A, the user has searched for the keyword "guilt." In response, the main panel displays the search result, which includes a hyperlinked timestamp and a hyperlinked word. Further, the replay panel provides a playback of the corresponding segment and a display of the speech context containing the corresponding word.

FIG. 4B depicts another exemplary visualization of the search result in the context of speech rate. As shown, the speech rate drops when the speaker talks about "guilt." This non-verbal cue may be indicative of a negative emotion, which corroborates the speaker's verbal expression.

Figure 4C:
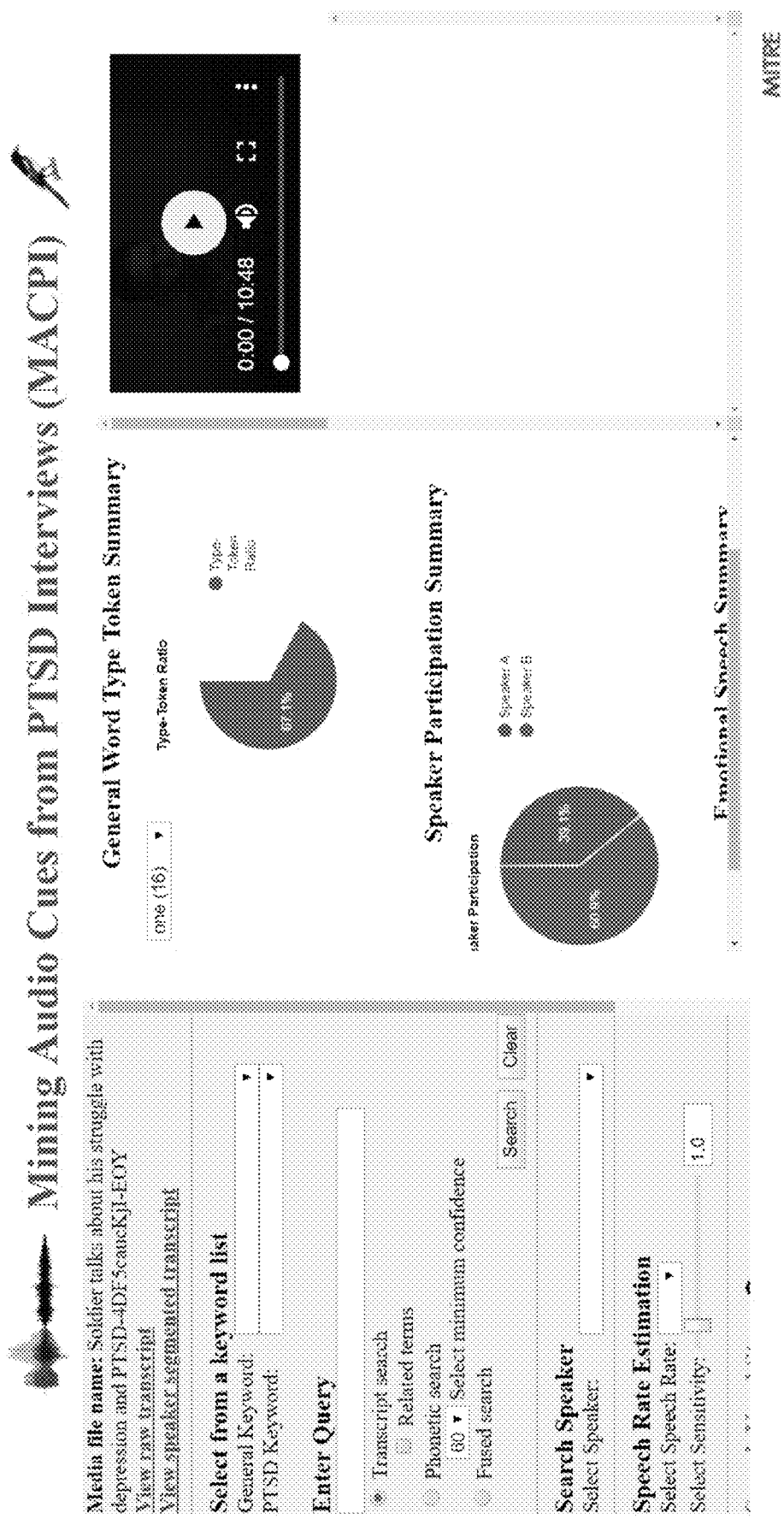
FIG. 4C depicts exemplary user interfaces of an electronic device in accordance with some embodiments.
Figure 4D:
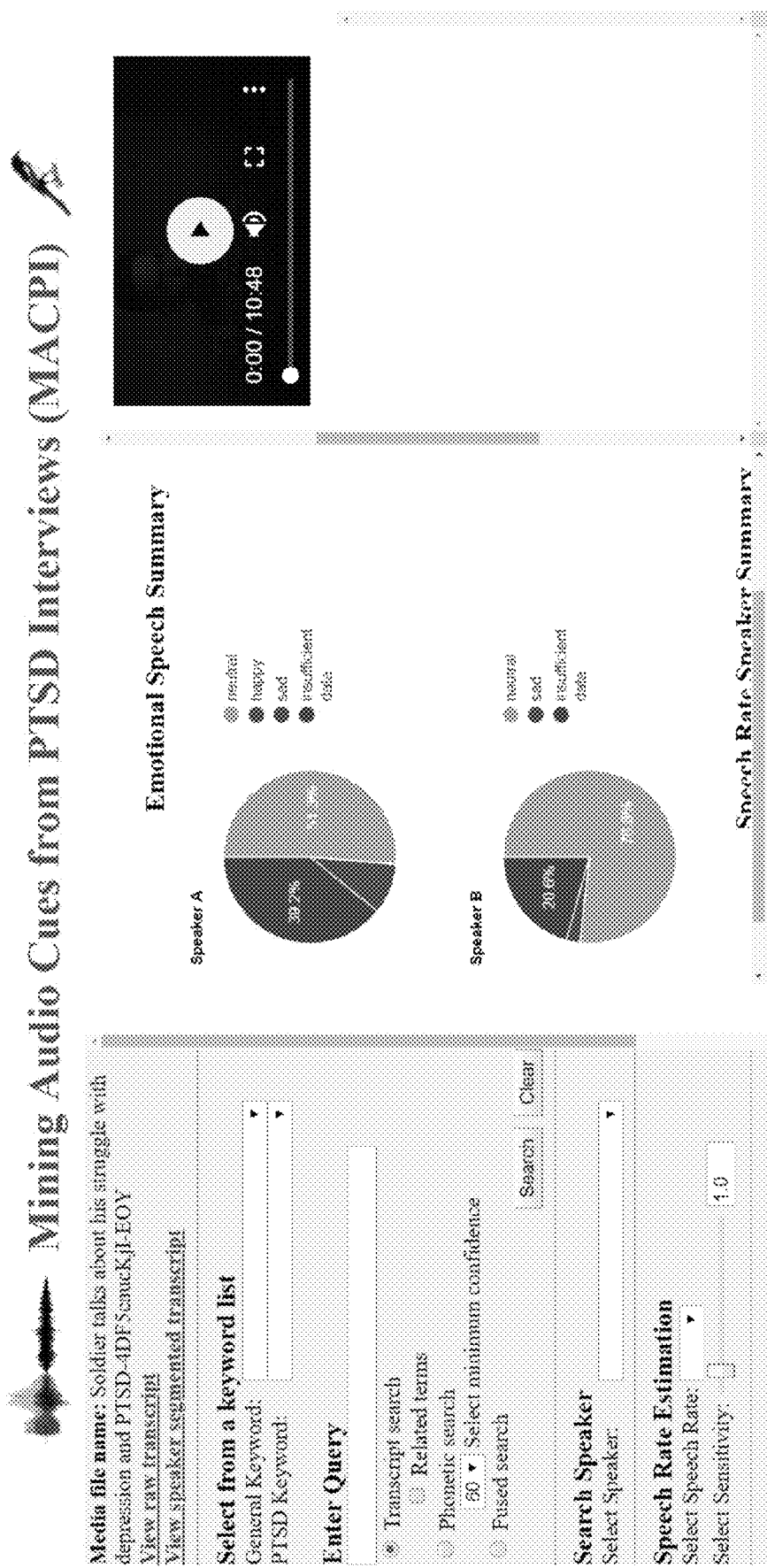
FIG. 4D depicts exemplary user interfaces of an electronic device in accordance with some embodiments.
Figure 4E:
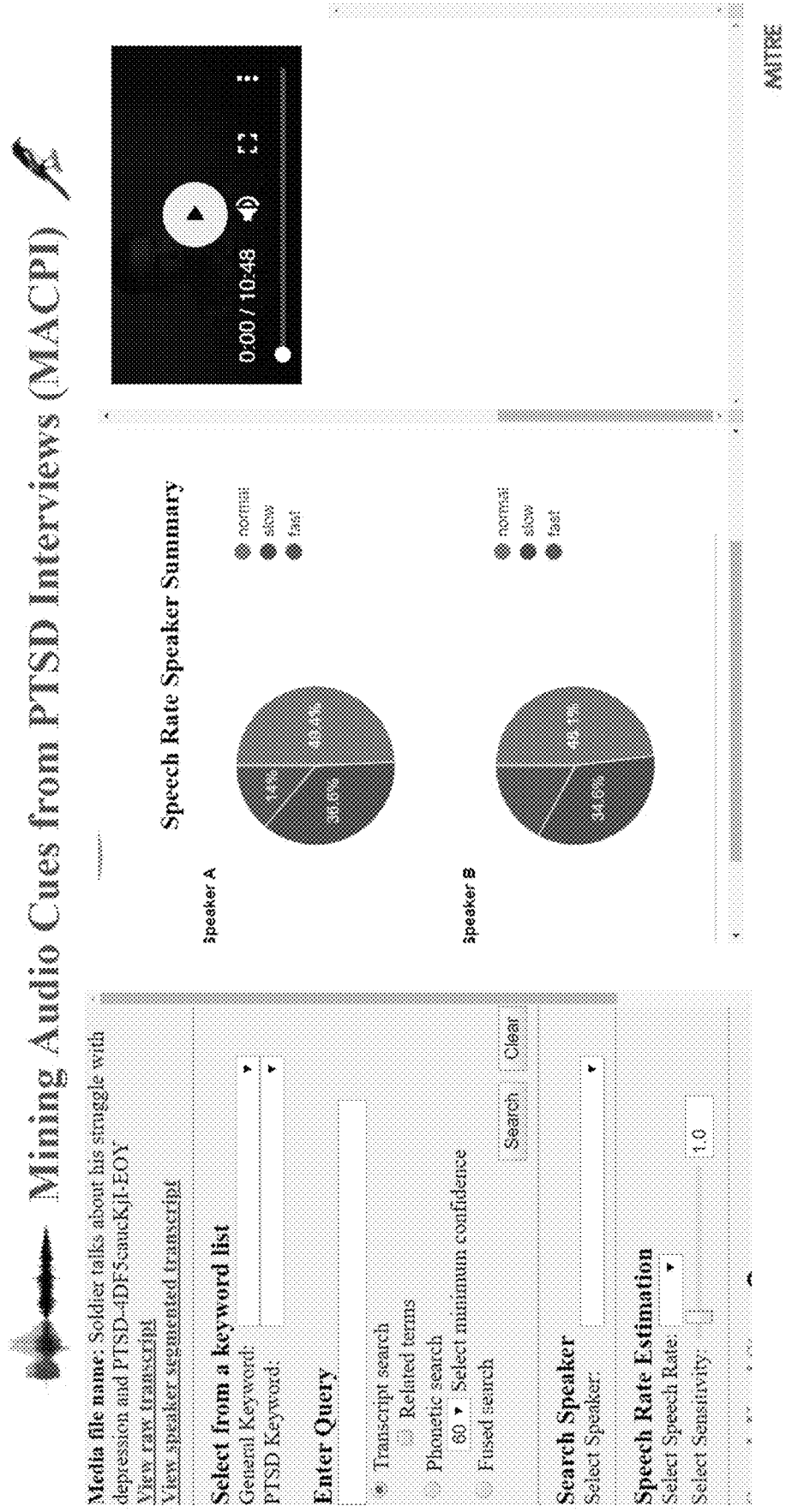
FIG. 4E depicts exemplary user interfaces of an electronic device in accordance with some embodiments.

FIGS. 4C-4E depict exemplary visualization of a process interview, in accordance with some embodiments of the invention. As shown in FIG. 4C, the user interface can provide a visualization of the type-token ratio for each speaker, which can indicate the education level and/or cognitive capability of each speaker. For example, a type-token ratio of 70% indicates a higher education level and/or higher cognitive capability than a type-token ratio of 20%, as it represents usage of a more diverse and complex vocabulary.

The user interface can also provide a visualization of speaker participation. Participation can be measured by the relative amount of the time each speaker spoke during the interview, the relative word count of each speaker during the interview, or a combination thereof.

As shown in FIG. 4D, the user interface can provide a visualization of an emotional speech summary for each speaker. For each speaker, the emotional speech summary can be determined by the time duration (or word count) associated with each detected emotion type. As shown, for Speaker A, the pie chart indicates that a significant portion of Speaker A's speech is associated with an emotion (or emotion type) of sadness.

As shown in FIG. 4E, the user interface can provide a visualization of a speech rate summary for each speaker. For each speaker, the user interface provides a pie chart illustrating the percentage of the conversation during which the speaker is speaking at a rate that is in the normal range, the slow range, and the fast range. The percentage can be calculated as a percentage of time, a percentage of word count, or a combination thereof.

Figure 4F:
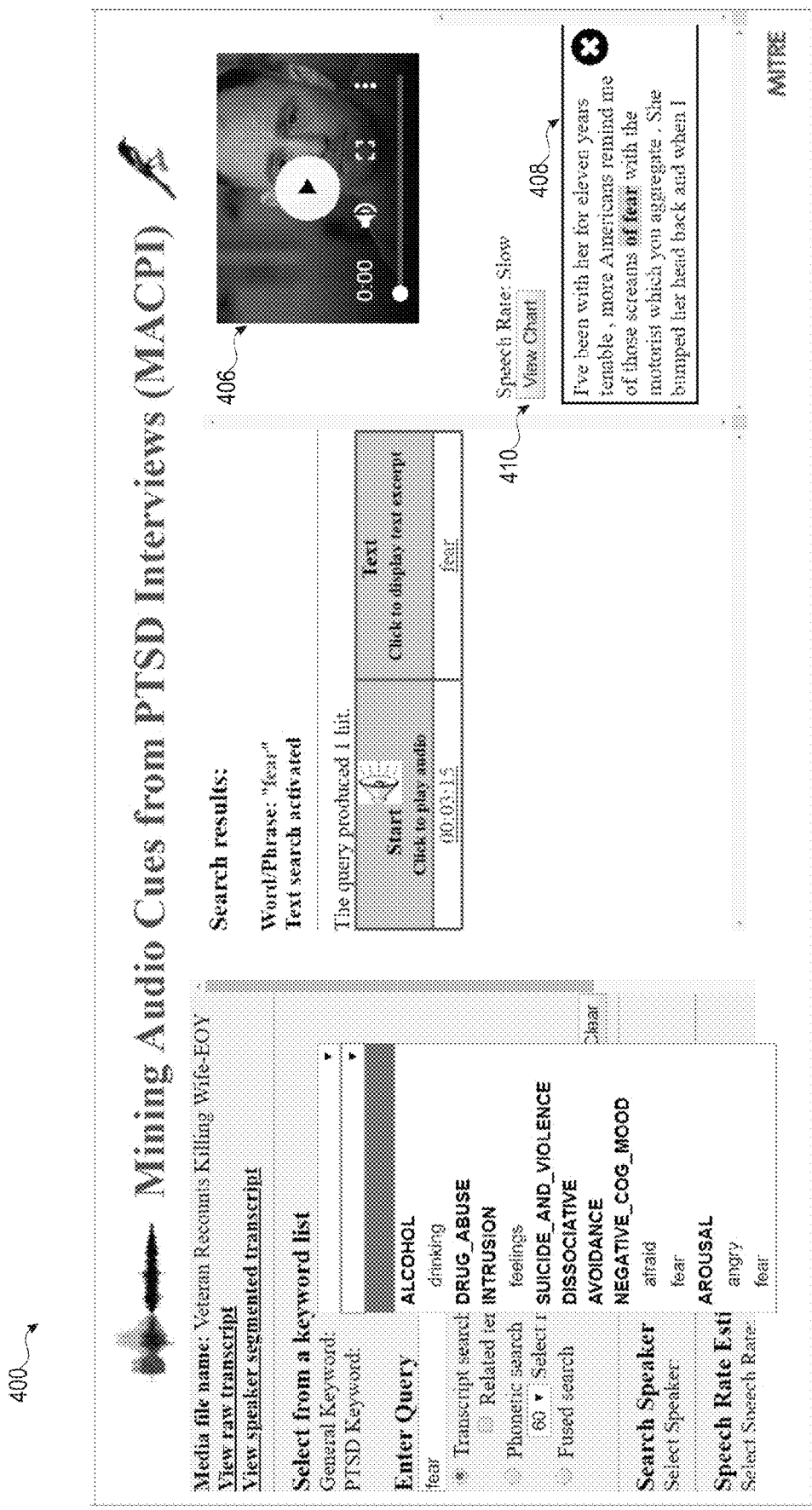
FIG. 4F depicts exemplary user interfaces of an electronic device in accordance with some embodiments.
Figure 4G:
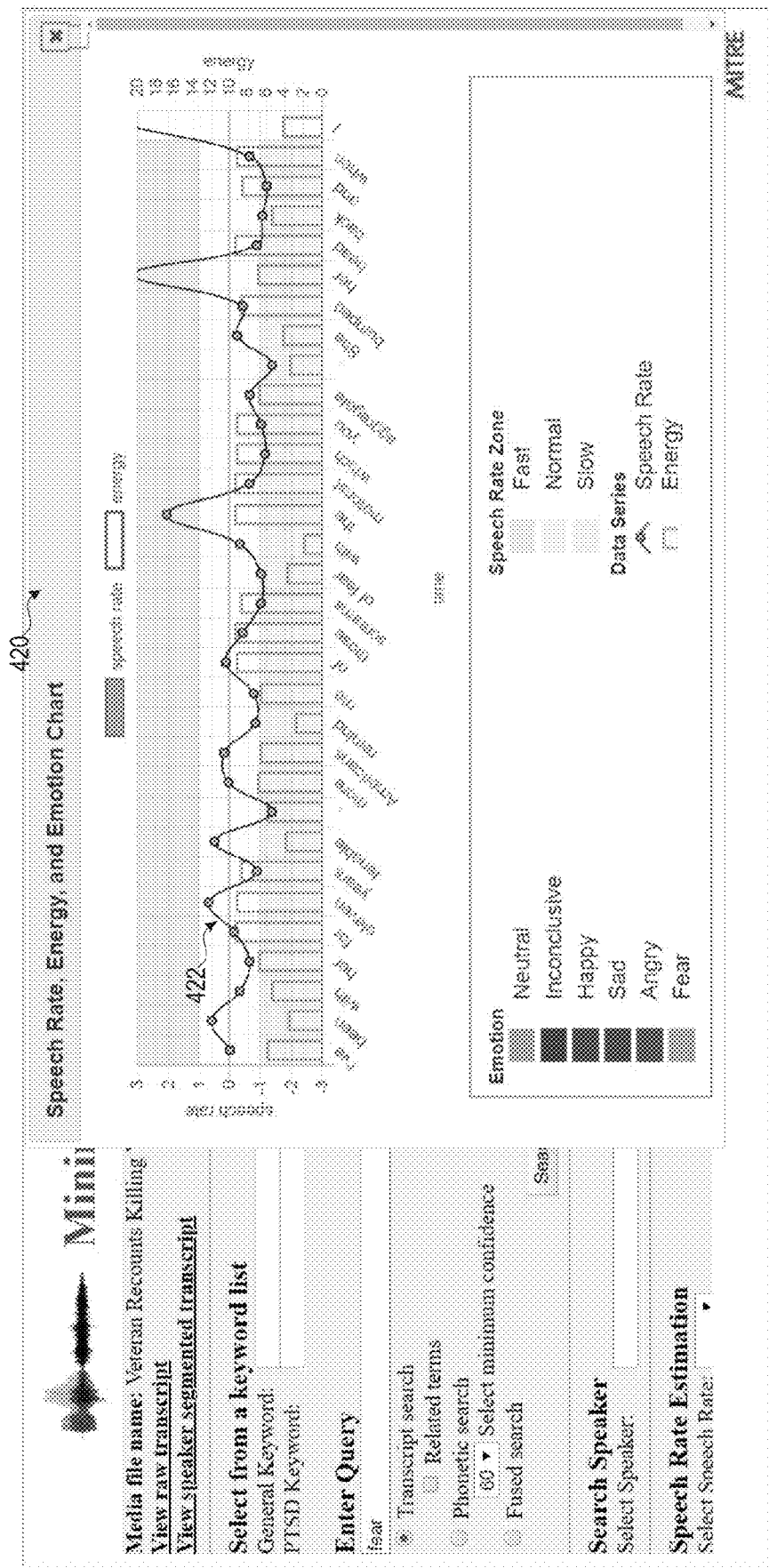
FIG. 4G depicts exemplary user interfaces of an electronic device in accordance with some embodiments.

FIGS. 4F-G depict exemplary user interfaces of an electronic device for reviewing an audio/video interview, in accordance with some embodiments of the invention. With reference to FIG. 4F, the user can search for portions of the interview by a list of general keywords or a list of PTSD keywords using the drop-down menus. The PTSD keywords (e.g., "drinking," "feelings," "afraid," "fear") are categorized for easier identification and selection. The user interface 400 also provides a text box such that the user can enter any query word. The user can further specify search settings, such as what type of search (e.g., transcript search with or without semantic extension, phonetic search with specific confidence threshold, fused search) to be performed.

In the depicted example, the user has conducted a transcript search for the word "fear," which returns one hit. The search result is provided to the user via two hyperlinks: a hyperlinked time stamp "00:03:15" and a hyperlinked word "fear." If the user selects the hyperlinked time stamp, the user interface 400 can provide a playback of a video or audio of the recording at the corresponding time, for example, via the video control 406. If the user selects the hyperlinked text, the user interface 400 can display a portion of the transcript that contains the query keyword, for example, via the text box 408. In some embodiments, the playback of the video is automatically synchronized with the display of the transcript. For example, the system can display a moving cursor in the text portion indicating the word being played back in the video. In some embodiments, the user can specify the length of the video (e.g., 10 seconds before and after the utterance of the query word "fear") or the length of the text portion (e.g., 15 words before and after the query word "fear") returned from his/her query.

The user interface 400 further provides a "View Chart" button 410 for accessing additional visualization options. One type of visualization is shown in FIG. 4G. The chart 420 visualizes a speaker's speech rate, energy, and emotion throughout the interview. As depicted, for each word, the speaker's speech rate throughout the interview is shown via the dots on the line 422. Further, for each word, the speaker's audio energy level is shown via the bar graph. If any emotion is detected at any point during the interview, the corresponding bar graph is color-coded accordingly. In the depicted example, the chart shows that when the speaker uttered "which" and "you," the emotion of fear is detected.

The chart 420 can display data at any level of granularity. For example, the chart can display a stream of syllables uttered by the speakers, as well as various metrics corresponding to each syllable such as speech rate, energy level, and detected emotion.

Returning to FIG. 4F, the user interface 400 can support searching by emotion or emotion types, which can retrieve all interview segments detected with the queried emotion type. The user interface 400 can also support searching by speech rate, which can retrieve all interview segments detected containing the queried speech rate.

The user interface 400 can support searching by any combination of search parameters. For example, the user interface can support searching by keywords and speaker to retrieve only the segments containing the keywords spoken by the speaker, searching by emotion types and speaker to retrieve only the segments containing the queries emotion by the queried speaker, searching by speech rate and speaker to retrieve only the segments containing the queried speech rate and the speaker.

Figure 5:
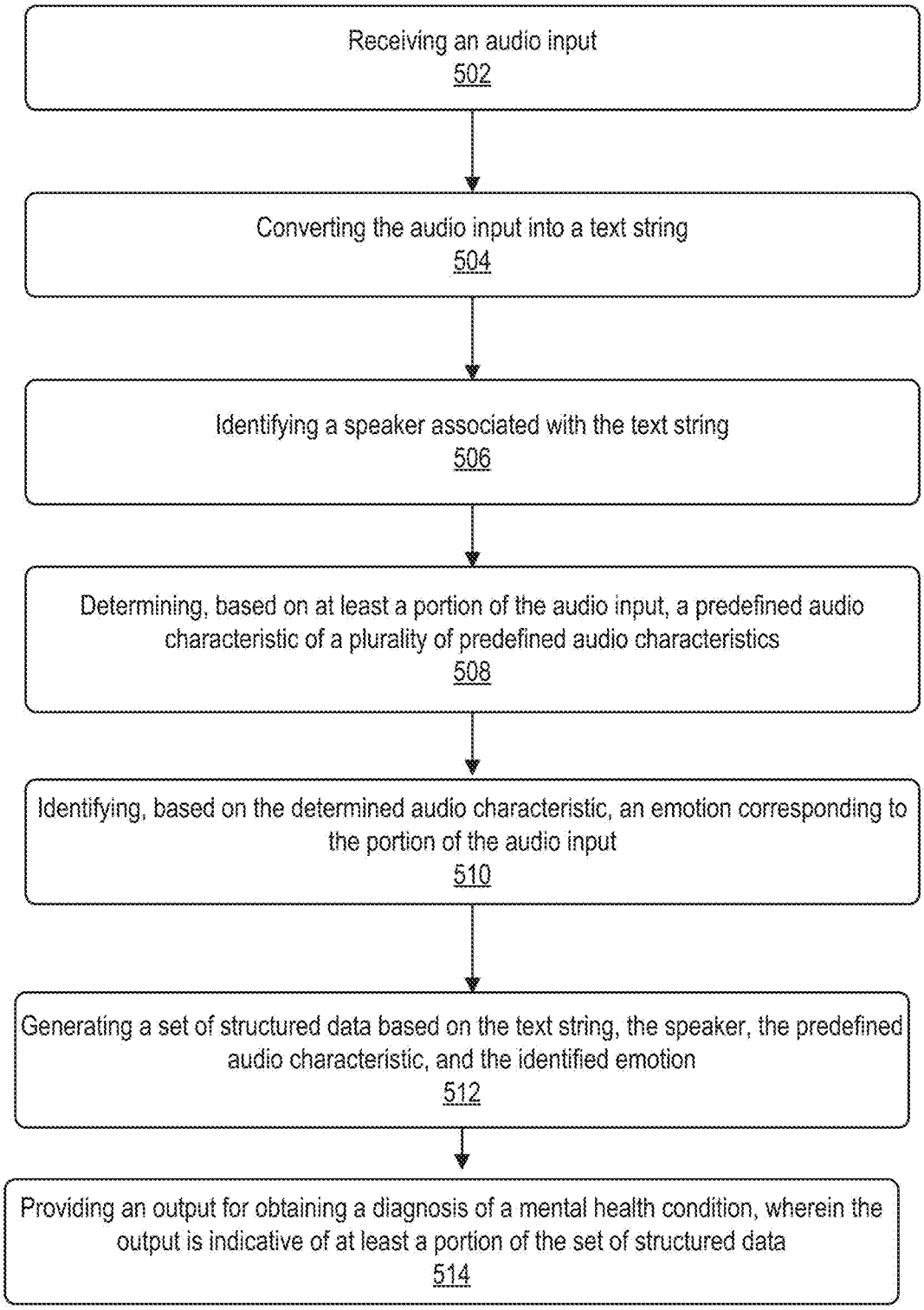
FIG. 5 depicts a block diagram of an exemplary process for processing audio data to diagnose mental health conditions, in accordance with some embodiments.

FIG. 5 illustrates process 500 for obtaining a diagnosis of a mental disorder or condition, according to various examples. Process 500 is performed, for example, using one or more electronic devices implementing a software platform. In some examples, process 500 is performed using a client-server system, and the blocks of process 500 are divided up in any manner between the server and a client device. In other examples, the blocks of process 500 are divided up between the server and multiple client devices. Thus, although portions of process 500 are described herein as being performed by particular devices of a client-server system, it will be appreciated that process 500 is not so limited. In other examples, process 500 is performed using only a client device or only multiple client devices. In process 500, some blocks are, optionally, combined, the order of some blocks is, optionally, changed, and some blocks are, optionally, omitted. In some examples, additional steps may be performed in combination with the process 500. Accordingly, the operations as illustrated (and described in greater detail below) are exemplary by nature and, as such, should not be viewed as limiting.

At block 502, the system receives an audio input. In some embodiments, the audio input includes one or more audio files. In some embodiments, the audio input is in a first format. The system converts the audio input into a predetermined format different from the first format (e.g., RAW).

At block 504, the system converts the audio input into a text string. In some embodiments, the conversion of the audio input into the text string is based on a commercial off-the-shelf algorithm, an open-source ASR software development kit ("SDK"), or a combination thereof.

At block 506, the system identifies a speaker (e.g., a patient being interviewed, a doctor) associated with the text string.

At block 508, the system, based on at least a portion of the audio input, determines a predefined audio characteristic of a plurality of predefined audio characteristics. In some embodiments, the predefined acoustic characteristic comprises speech rate, pitch, intonation, energy level, or a combination thereof. In some embodiments, the determination is based on metadata associated with the audio input. At block 510, the system, based on the determined audio characteristic, identifies an emotion corresponding to the portion of the audio input.

In some embodiments, the system detects an indicator of the mental disorder or condition based on a portion of the text string. In some embodiments, detecting the indicator of the mental disorder or condition comprises detecting one or more predefined words in the portion of the text string. In some embodiments, detecting the indicator of the mental disorder or condition comprises: providing the portion of the text string to a classifier; and receiving, from the classifier, the indicator of the mental disorder or condition. In some embodiments, the indicator includes a speech pattern.

At block 512, the system generates a set of structured data based on the text string, the speaker, the predefined audio characteristic, and the identified emotion. In some embodiments, generating a set of structured data based on the text string, the speaker, the predefined audio characteristic, and the identified emotion comprises: associating a portion of the text string with the speaker, the predefined audio characteristic, the identified emotion, or a combination thereof. In some embodiments, generating a set of structured data based on the text string, the speaker, the predefined audio characteristic, and the identified emotion comprises: associating the portion of the audio input with the speaker, the predefined audio characteristic, the identified emotion, or a combination thereof.

At block 514, the system provides an output for obtaining the diagnosis of the mental disorder or condition, wherein the output is indicative of at least a portion of the set of structured data. In some embodiments, the system receives a user input indicative of a query for a keyword. In some embodiments, the system, in response to receiving the user input, provides an output indicative of a segment of the audio input.

Figure 6:
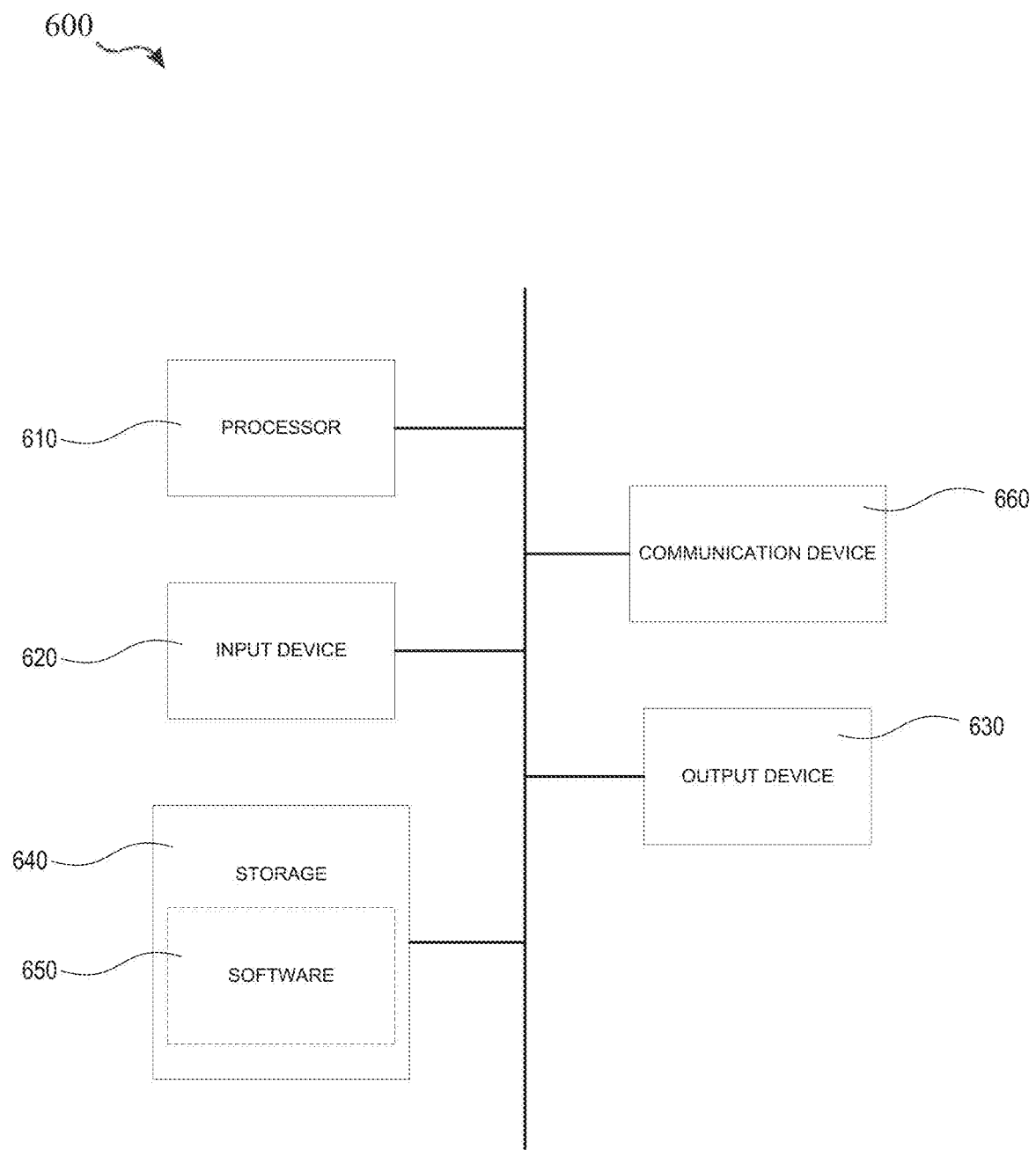
FIG. 6 depicts an exemplary electronic device in accordance with some embodiments.

The operations described above with reference to FIG. 5 are optionally implemented by components depicted in FIG. 6. It would be clear to a person having ordinary skill in the art how other processes are implemented based on the components depicted in FIGS. 1-4B and 6.

FIG. 6 illustrates an example of a computing device in accordance with one embodiment. Device 600 can be a host computer connected to a network. Device 600 can be a client computer or a server. As shown in FIG. 6, device 600 can be any suitable type of microprocessor-based device, such as a personal computer, workstation, server or handheld computing device (portable electronic device) such as a phone or tablet. The device can include, for example, one or more of processor 610, input device 620, output device 630, storage 640, and communication device 660. Input device 620 and output device 630 can generally correspond to those described above, and they can either be connectable or integrated with the computer.

Input device 620 can be any suitable device that provides input, such as a touch screen, keyboard or keypad, mouse, or voice-recognition device. Output device 630 can be any suitable device that provides output, such as a touch screen, haptics device, or speaker.

Storage 640 can be any suitable device that provides storage, such as an electrical, magnetic or optical memory including a RAM, cache, hard drive, or removable storage disk. Communication device 660 can include any suitable device capable of transmitting and receiving signals over a network, such as a network interface chip or device. The components of the computer can be connected in any suitable manner, such as via a physical bus or wirelessly.

Software 650, which can be stored in storage 640 and executed by processor 610, can include, for example, the programming that embodies the functionality of the present disclosure (e.g., as embodied in the devices as described above).

Software 650 can also be stored and/or transported within any non-transitory computer-readable storage medium for use by or in connection with an instruction execution system, apparatus, or device, such as those described above, that can fetch instructions associated with the software from the instruction execution system, apparatus, or device and execute the instructions. In the context of this disclosure, a computer-readable storage medium can be any medium, such as storage 640, that can contain or store programming for use by or in connection with an instruction execution system, apparatus, or device.

Software 650 can also be propagated within any transport medium for use by or in connection with an instruction execution system, apparatus, or device, such as those described above, that can fetch instructions associated with the software from the instruction execution system, apparatus, or device and execute the instructions. In the context of this disclosure, a transport medium can be any medium that can communicate, propagate or transport programming for use by or in connection with an instruction execution system, apparatus, or device. The transport readable medium can include, but is not limited to, an electronic, magnetic, optical, electromagnetic or infrared wired or wireless propagation medium.

Device 600 may be connected to a network, which can be any suitable type of interconnected communication system. The network can implement any suitable communications protocol and can be secured by any suitable security protocol. The network can comprise network links of any suitable arrangement that can implement the transmission and reception of network signals, such as wireless network connections, T1 or T3 lines, cable networks, DSL, or telephone lines.

Device 600 can implement any operating system suitable for operating on the network. Software 650 can be written in any suitable programming language, such as C, C++, Java or Python. In various embodiments, application software embodying the functionality of the present disclosure can be deployed in different configurations, such as in a client/server arrangement or through a Web browser as a Web-based application or Web service, for example.

Although the disclosure and examples have been fully described with reference to the accompanying figures, it is to be noted that various changes and modifications will become apparent to those skilled in the art. Such changes and modifications are to be understood as being included within the scope of the disclosure and examples as defined by the claims.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described to best explain the principles of the techniques and their practical applications. Others skilled in the art are thereby enabled to best utilize the techniques and various embodiments with various modifications as are suited to the particular use contemplated.

What is claimed is:

1. A computer-enabled method for obtaining a diagnosis of a mental health disorder or condition, the method comprising:
receiving an audio input;
sampling the received audio input by one or more microphones to generate an electrical audio signal;
converting the audio signal into a text string;
identifying a speaker associated with the text string;
detecting an indicator of the mental health condition based on a portion of the text string, wherein detecting the indicator of the mental disorder or condition comprises:
applying a machine learning classifier to the portion of the text string and generating from the classifier an indicator of the mental health condition, wherein the machine learning classifier includes a neural network generated using training data, the training data comprising a plurality of audio inputs previously associated with a known mental health condition;
determining, based on at least a portion of the audio signal, a predefined audio characteristic of a plurality of predefined audio characteristics, wherein determining the predefined audio characteristic comprises determining one or more electrical properties of the electrical audio signal;
identifying, based on the determined audio characteristic of the plurality of predefined audio characteristics corresponding to the portion of the audio input, an emotion corresponding to the portion of the audio input;

generating a set of structured data based on the text string, the detected indicator of the mental health condition, the speaker, the predefined audio characteristic, and the identified emotion, wherein the generated set of structured data is configured to enable cross-modality search and retrieval of the text string, the speaker, the predefined audio characteristic, and the identified emotion; and generating a visualization at a display based on the generated set of structured data, wherein the generated visualization comprises an index of a plurality of user selectable keywords, wherein at least one of the plurality of user selectable keywords is associated in the index with the detected indicator of the mental health condition based on a relationship between the at least one keyword and the detected indicator of the mental health condition, and wherein the index is configured to enable search of the structured data based on a keyword of the plurality of user selectable keywords.

2. The method according to claim 1, wherein the mental condition is PTSD.

3. The method according to claim 1, wherein the audio input includes one or more audio files.

4. The method according to claim 1, wherein the audio input is in a first format, the method further comprising: converting the audio input into a predetermined format different from the first format.

5. The method according to claim 1, wherein the conversion of the audio input into the text string is based on a commercial off-the-shelf algorithm, an open-source ASR software development kit ("SDK"), or a combination thereof.

6. The method according to claim 1, wherein detecting the indicator of the mental disorder or condition comprises detecting one or more predefined words in the portion of the text string.

7. The method according to claim 1, wherein the indicator includes a speech pattern.

8. The method according to claim 1, wherein the predefined acoustic characteristic comprises speech rate, pitch, intonation, energy level, or a combination thereof.

9. The method according to claim 1, wherein generating a set of structured data based on the text string, the detected indicator of the mental health condition, the speaker, the predefined audio characteristic, and the identified emotion comprises: associating a portion of the text string with the speaker, the predefined audio characteristic, the identified emotion, or a combination thereof.

10. The method according to claim 1, wherein generating a set of structured data based on the text string, the speaker, the predefined audio characteristic, and the identified emotion comprises: associating the portion of the audio input with the speaker, the predefined audio characteristic, the identified emotion, or a combination thereof.

11. The method according to claim 1, further comprising: receiving a user input indicative of a query for a keyword.

12. The method according to claim 11, further comprising: in response to receiving the user input, providing an output indicative of a segment of the audio input.

13. The method according to claim 12, wherein receiving the user input comprises receiving a selection of a user selectable keyword of the plurality of user selectable keywords.

14. The method according to claim 13, wherein the output indicative of a segment of the audio input comprises at least one of a video comprising the keyword, a portion of the text string comprising the keyword, a timestamp associated with the keyword, and a hyperlink associated with the keyword.

15. The method of claim 1, wherein the keywords are determined based on at least one of the text string and the audio signal.

16. An electronic device, comprising:
a display;
one or more processors;
a memory; and
one or more programs, wherein the one or more programs are stored in the memory and configured to be executed by the one or more processors, the one or more programs including instructions for:
receiving an audio input;
sampling the received audio input by one or more microphones to generate an electrical audio signal;
converting the audio signal into a text string;
identifying a speaker associated with the text string;
detecting an indicator of the mental health condition based on a portion of the text string, wherein detecting the indicator of the mental disorder or condition comprises:
applying a machine learning classifier to the portion of the text string and generating from the classifier an indicator of the mental health condition, wherein the machine learning classifier includes a neural network generated using training data, the training data comprising a plurality of audio inputs previously associated with a known mental health condition;
determining, based on at least a portion of the audio signal, a predefined audio characteristic of a plurality of predefined audio characteristics, wherein determining the predefined audio characteristic comprises determining one or more electrical properties of the electrical audio signal;
identifying, based on the determined audio characteristic of the plurality of predefined audio characteristics corresponding to the portion of the audio input, an emotion corresponding to the portion of the audio input;
generating a set of structured data based on the text string, the detected indicator of the mental health condition, the speaker, the predefined audio characteristic, and the identified emotion, wherein the generated set of structured data is configured to enable cross-modality search and retrieval of the text string, the speaker, the predefined audio characteristic, and the identified emotion; and
generating a visualization at a display based on the generated set of structured data, wherein the generated visualization comprises an index of a plurality of user selectable keywords, wherein at least one of the plurality of user selectable keywords is associated in the index with the detected indicator of the mental health condition based on a relationship between the at least one keyword and the detected indicator of the mental health condition, and wherein the index is configured to enable search of the structured data based on a keyword of the plurality of user selectable keywords.

17. A non-transitory computer-readable storage medium storing one or more programs, the one or more programs comprising instructions, which when executed by one or more processors of an electronic device having a display, cause the electronic device to:

receive an audio input;
sample the received audio input by one or more microphones to generate an electrical audio signal;
convert the audio signal into a text string;
identify a speaker associated with the text string;
detect an indicator of the mental health condition based on a portion of the text string, wherein detecting the indicator of the mental disorder or condition comprises:
  applying a machine learning classifier to the portion of the text string and generating from the classifier an indicator of the mental health condition, wherein the machine learning classifier includes a neural network generated using training data, the training data comprising a plurality of audio inputs previously associated with a known mental health condition;
determine, based on at least a portion of the audio signal, a predefined audio characteristic of a plurality of predefined audio characteristics, wherein determining the predefined audio characteristic comprises determining one or more electrical properties of the electrical audio signal;
identify, based on the determined audio characteristic of the plurality of predefined audio characteristics corresponding to the portion of the audio input, an emotion corresponding to the portion of the audio input;
generate a set of structured data based on the text string, the detected indicator of the mental health condition, the speaker, the predefined audio characteristic, and the identified emotion, wherein the generated set of structured data is configured to enable cross-modality search and retrieval of the text string, the speaker, the predefined audio characteristic, and the identified emotion; and
generate a visualization at a display based on the generated set of structured data, wherein the generated visualization comprises an index of a plurality of user selectable keywords, wherein at least one of the plurality of user selectable keywords is associated in the index with the detected indicator of the mental health condition based on a relationship between the at least one keyword and the detected indicator of the mental health condition, and wherein the index is configured to enable search of the structured data based on a keyword of the plurality of user selectable keywords.

* * * * *